United States Patent
Zeng et al.

(10) Patent No.: US 7,912,661 B2
(45) Date of Patent: Mar. 22, 2011

(54) IMPEDANCE ANALYSIS TECHNIQUE FOR FREQUENCY DOMAIN CHARACTERIZATION OF MAGNETOELASTIC SENSOR ELEMENT BY MEASURING STEADY-STATE VIBRATION OF ELEMENT WHILE UNDERGOING CONSTANT SINE-WAVE EXCITATION

(75) Inventors: Kefeng Zeng, Mantua, NJ (US); Keat Ghee Ong, Houghton, MI (US); Xiping Yang, Dallas, TX (US); Craig A. Grimes, Boalsburg, PA (US)

(73) Assignee: KMG2 Sensors Corporation, Boalsburg, PA (US)

( * ) Notice: Subject to any disclaimer, the term of this patent is extended or adjusted under 35 U.S.C. 154(b) by 513 days.

(21) Appl. No.: 11/710,294

(22) Filed: Feb. 23, 2007

(65) Prior Publication Data
US 2008/0071487 A1 Mar. 20, 2008

Related U.S. Application Data

(60) Provisional application No. 60/787,945, filed on Mar. 31, 2006.

(51) Int. Cl.
*G01R 23/16* (2006.01)
(52) U.S. Cl. ......... 702/76; 702/56; 702/189; 324/76.11; 324/600
(58) Field of Classification Search .......... 702/109–127, 702/189–199, 76, 56; 361/139–210; 324/200–263, 324/600–727, 76.11–76.83, 525, 117 R
See application file for complete search history.

(56) References Cited

U.S. PATENT DOCUMENTS 5,295,084 A * 3/1994 Arunachalam et al.
(Continued)

OTHER PUBLICATIONS

Grimes, C.A., K G. Ong, et al, "Magnetoelastic sensors for remote query environment monitoring, "Journal of Smart Materials and Structures, vol. 8, (1999) 639-646, printed in the UK; listed in applicants' specification.

(Continued)

*Primary Examiner* — Mohamed Charioui
*Assistant Examiner* — Ricky Ngon
(74) *Attorney, Agent, or Firm* — Macheledt Bales LLP

(57) ABSTRACT

Circuitry and program code adapted for carrying out an associated technique for characterizing the response of one or more magnetoelastic sensor elements during exposure to an excitation field generated by an interrogation coil: including: (a) measuring a total sensor signal from the coil with the sensor element positioned within the excitation field within a spacing created by a winding of the coil; and (b) automatically determining: (i) a total measured impedance spectrum from said total sensor signal so measured, and (ii) a plurality of magnitude values representing the real part of a reconstructed impedance spectrum for the sensor element. The reconstructed impedance spectrum for the sensor element, having been calculated by subtracting an impedance generally attributable to the coil during the time an AC excitation signal is provided, from the total measured impedance. Subtraction of coil impedance from total complex impedance is accomplished by separate subtraction of the real part and of the imaginary part, represented as follows $$Re[Z_s(\omega)] = Re[Z_t(\omega)] - Re[Z_c(\omega)] \qquad \text{Equation (12)}$$

and $$Im[Z_s(\omega)] = Im[Z_t(\omega)] - Im[Z_c(\omega)] \qquad \text{Equation (13)}$$

where subscript "t" indicates total complex impedance, "s" indicates sensor element impedance, and "c" indicates coil impedance.

20 Claims, 12 Drawing Sheets

U.S. PATENT DOCUMENTS

| | | | |
|---|---|---|---|
| 5,629,209 A * | 5/1997 | Braun, Sr. et al. | |
| 6,359,444 B1 * | 3/2002 | Grimes | 324/633 |
| 6,393,921 B1 * | 5/2002 | Grimes et al. | |
| 6,397,661 B1 * | 6/2002 | Grimes et al. | |
| 6,586,946 B2 * | 7/2003 | Hefti et al. | 324/636 |
| 6,639,402 B2 * | 10/2003 | Grimes et al. | |
| 6,688,162 B2 * | 2/2004 | Bachas et al. | 73/64.42 |
| 6,815,947 B2 * | 11/2004 | Scheiner et al. | 324/230 |
| 6,861,852 B2 * | 3/2005 | Slates | 324/699 |
| 7,113,876 B2 * | 9/2006 | Zeng et al. | |
| 2001/0054896 A1 * | 12/2001 | Mednikov et al. | 324/225 |
| 2004/0061511 A1 * | 4/2004 | Kawakatsu | 324/707 |
| 2005/0192765 A1 * | 9/2005 | Slothers et al. | 702/57 |
| 2006/0071658 A1 * | 4/2006 | Mednikov et al. | 324/207.17 |

OTHER PUBLICATIONS

K Zeng, K.G. Ong, C. Mungle, and C A. Grimes, "Time domain characterization of oscillating sensors; Application of frequency counting to resonance frequency determination," Rev. Sci. Instruments vol. 73, 4375-4380 (Dec. 2002); listed in applicants' specification.

Jain, M.K., C. A. Grimes, "A Wireless Magnetoelastic Micro-Sensor Array for Simultaneous Measurement of Temperature and Pressure," IEEE Transaction on Magnetics, vol. 37, No. 4, pp. 2022-2024, 2001; listed in applicants ' Specification.

H Reindl, et al. "Theory and Application of Passive SAW Radio Transporters as Sensors," IEEE Transactions on Ultrasonics, Ferroelectrics, and Frequency Control, vol. 45, No. 5, (Sep. 1998).

* cited by examiner

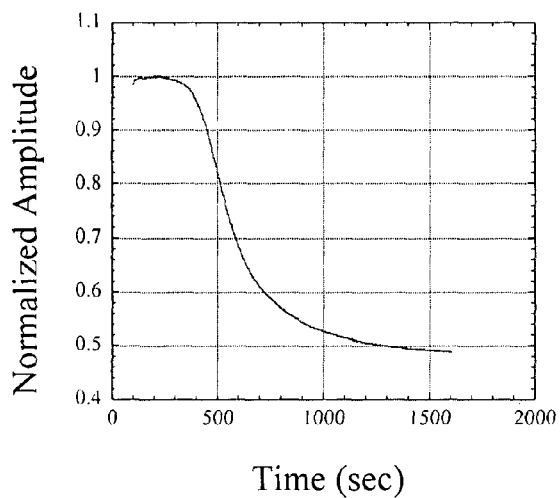
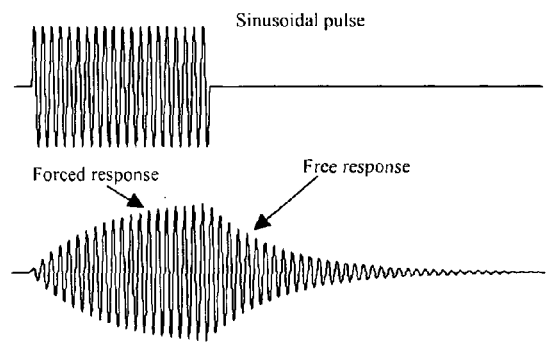
Figure 25
Figure 26
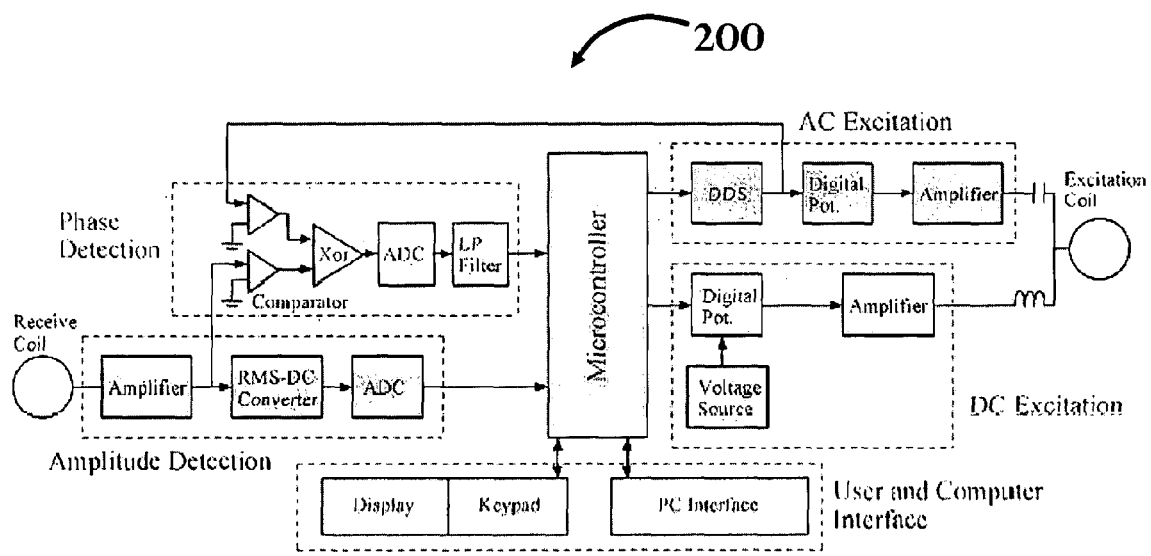
Figure 27

IMPEDANCE ANALYSIS TECHNIQUE FOR FREQUENCY DOMAIN CHARACTERIZATION OF MAGNETOELASTIC SENSOR ELEMENT BY MEASURING STEADY-STATE VIBRATION OF ELEMENT WHILE UNDERGOING CONSTANT SINE-WAVE EXCITATION

BACKGROUND OF THE INVENTION

This application claims the benefit of pending U.S. provisional patent application No. 60/787,945 filed 31 Mar. 2006 for the applicants on behalf of the assignee hereof.

FIELD OF THE INVENTION

In general, the present invention relates to techniques for characterizing emissions from resonator-type sensor elements such as magnetoelastic resonant sensor elements, quartz crystal microbalance (QCM) elements, piezoelectric acoustic wave elements, and so on—to gain useful information from the sensor element(s) about an environment, analyte or sample of interest. These resonator-type elements each vibrate in response to sine wave excitation and impulse excitation. Magnetoelastic sensors belong to the broad class of sensors sometimes referred to as resonator sensors. Resonator sensors are those that can be described as having characteristics similar to those exhibited by an LC oscillation circuit. The invention is directed to a novel, improved impedance analysis technique applied to measure the steady-state vibration of a magnetoelastic sensor element forced by a constant sine wave excitation, as opposed to the threshold-crossing counting technique invented earlier and detailed in U.S. Pat. No. 7,113,876 filed 8 Sep. 2004 and granted to three co-applicants hereof (Drs. K. Zeng, K. G. Ong, and C. A. Grimes) and entitled "Technique and Electronic Circuitry for Quantifying a Transient Signal using Threshold-crossing Counting to Track Signal Amplitude."

As explained in U.S. Pat. No. 7,113,876, fully incorporated herein by reference for its technical background discussion, this earlier threshold-crossing counting technique—very generally stated—measures free vibration of a sensor element once excitation of the element has stopped. The patented circuitry and technique includes a threshold comparison feature employing the transient signal received (which had been emitted as a result of the sensor element vibrations), coined by applicants as 'threshold-crossing counting.' The unique technique to which the instant application is directed, does not employ threshold-crossing counting (and needs no threshold comparison circuitry); but rather, sensor resonance behavior is characterized in the frequency domain, after having obtained the complex (magnitude, phase) impedance spectrum of the sensor element. While applicants' prior threshold-crossing counting technique is useful in a wide range of environments, as reported, this new technique can provide superior results, especially in viscous environments where the medium through which the sensor emissions must 'ring' in order to provide sensor information, is viscous.

The electronic implementation designed for the new technique to which the instant application is directed, employs single circuit board embedded system that, when interfaced with a computer (such as a personal computer, PC), uses a single solenoid coil to characterize sensor resonance behavior in the frequency domain by obtaining the complex (magnitude, phase) impedance spectrum for the sensor element from a measured impedance (a 'combined' impedance for the system of sensor element plus coil). As uniquely conceived, the coil impedance (coil without the sensor element) is subtracted from a measured ('combined' system) impedance to provide the impedance spectrum that characterizes the sensor element resonant behavior, and from which useful information about an environment, analyte or sample of interest, is gleaned. The example/model system disclosed herein nicely predicts the measured-sensor spectrum obtained experimentally. The new impedance technique has been applied to endotoxin detection (i.e., detection of some pathogen or constituent thereof) and blood coagulation monitoring, by way of example only. A wide variety of applications of the unique technique are contemplated, as one will appreciate. The unique concept of design of the electronic circuitry permits flexibility of hardware implementation and associated automatic control thereof. The unique system and technique provides a simple, low-cost, and functional agile enabling tool for practical use of this very novel sensor technology.

1. Introduction

Magnetoelastic sensor technology is an application of magnetostriction, also known as the Joule effect, a phenomenon typically observed in magnetostrictive materials that, when exposed to an applied magnetic field, exhibit bi-directional energy exchange between magnetic and elastic states. Magnetoelastic sensors belong to the broad class of resonator sensors, and are analogous to piezoelectric sensors such as quartz crystal microbalance (QCM) sensors and surface-acoustic-wave (SAW) sensors. While piezoelectric sensors are generally excited using capacitive electrodes, the magnetoelastic sensors are excited using inductive coils, making sensor interrogation inherently non-contact. The magnetoelastic sensors, used by way of example for purposes of illustration herein, were comprised of commercially available Metglas thick film, alloy 2826MB, typically shear- or laser-cut into rectangular ribbon-like plates. When magnetically excited, a magnetoelastic sensor exhibits a longitudinal elastic vibration, described by the equation of motion:

$$\frac{\partial^2 u(x,t)}{\partial t^2} = \frac{E}{\rho}\frac{\partial^2 u(x,t)}{\partial x^2} \qquad (1)$$

where $\rho$ is the mass density and E is the Young's modulus. Solving the equation of motion yields a fundamental resonance frequency, $f_r$, given by $$f_r = \frac{1}{2L}\sqrt{\frac{E}{\rho}} \qquad \text{Equation (2)}$$

where L is the sensor length. Mass-loading the sensor will cause a change in mass density $\rho$ and hence a shift in the resonance frequency. For a small mass load $\Delta m$ evenly deposited on a sensor of mass $m_o$, the frequency shift is calculated by:

$$\Delta f = -f_r \frac{\Delta m}{2m_o} \qquad \text{Equation (3)}$$

Chemical or biological (sometimes denoted herein as 'chem/bio') sensors can be fabricated by adhering a mass-changing analyte responsive layer to the surface of the magnetoelastic sensor. In addition to chem/bio sensing applications, the resonance behavior of a magnetoelastic sensor element also responds to changes in physical properties/parameters including pressure, temperature, liquid density and viscosity, as well as fluid flow velocity.

This new sensor platform is suitable for those applications where relatively fast and accurate sensor characterization is sought, such that sensor resonance behavior in the time domain or the frequency domain may be tracked. In applicants' previous work as mentioned above, threshold-crossing counting was utilized to analyze the transient characteristics of pulse-wise excited sensor response. Here, an impedance spectrum analysis technique is applied for sensor element characterization; along with an electronic implementation thereof employing a single embedded circuit board interfaced with a processor unit (e.g., whether located within a palmtop, laptop, handheld, remote hard-wired, remote wireless, and so on) to perform a novel impedance spectrum analysis.

2. General Discussion of Assorted Technological Areas:

I. Excitation of resonator-type sensing elements. In earlier patented work, one of which is entitled "Magnetoelastic Sensor for Characterizing Properties of Thin-film/Coatings" U.S. Pat. No. 6,688,162, one or more of the applicants hereof detail the excitation of magnetoelastic elements, in operation as sensing units:

When a sample of magnetoelastic material is exposed to an alternating magnetic field, it starts to vibrate. This external time-varying magnetic field can be a time-harmonic signal or a non-uniform field pulse (or several such pulses transmitted randomly or periodically). If furthermore a steady DC magnetic field is superimposed to the comparatively small AC magnetic field, these vibrations occur in a harmonic fashion, leading to the excitation of harmonic acoustic waves inside the sample. The mechanical oscillations cause a magnetic flux change in the material due to the inverse magnetoelastic effect. These flux changes, in unison with the mechanical vibrations, can be detected in a set of EM emission pick-up coils. The vibrations of the sample are largest if the frequency of the exciting field coincides with the characteristic acoustic resonant frequency of the sample. Thus, the magnetoelastic resonance frequency detectable by an EM pick-up coil coincides with the frequency of the acoustic resonance. And, sensor element emissions can be detected acoustically, for example by a remote microphone/hydrophone or a piezoelectric crystal, by detecting the acoustic wave generated from the mechanical vibrations of the sensor. A relative-maximum response of the emissions remotely measured is identified to determine the sensing element's characteristic resonant frequency. The emissions from a sensing element of the invention can also be monitored optically whereby amplitude modulation of a laser beam reflected from the sensor surface is detected. Signal processing of the sensor elements can take place in the frequency-domain or in the time-domain using a field-pulse excitation.

FIG. 1A schematically depicts components of an apparatus and method of the invention for remote query of a thin-film layer or coating 14 atop a base magnetostrictive element 12. A time-varying magnetic field 17 is applied to sensor element 10, with a layer/coating 14 of interest having been deposited onto a surface of the base 14, by way of a suitable drive coil 16 such that emissions 19 from the sensor element can be picked-up by a suitable pick-up coil 18. Two useful ways to measure the frequency spectrum include: frequency domain measurement and the time domain measurement. In the frequency domain measurement, the sensing element's vibration is excited by an alternating magnetic field of a monochromatic frequency. The amplitude of the sensor response is then registered while sweeping ('listening') over a range of frequencies that includes the resonance frequency of the sensor element. Finding the maximum amplitude of the sensor response leads to the characteristic resonant frequency. FIG. 1B graphically depicts interrogation field transmissions from a drive coil (SEND) in both the frequency domain 22 and in the time-domain 26 (an impulse of, say, 200 A/m and 8 µs in duration). The transient response (emissions) captured 27 is converted to frequency domain 28 using a FFT to identify a resonant frequency. [end quote]

II. Applications/uses of resonator-type sensing elements. Tracking the resonant behavior of magnetoelastic resonator sensors has enabled physical property measurements including pressure, temperature, liquid density and viscosity, and fluid flow velocity and direction. Furthermore in combination with functional surfaces that change mass or elasticity in response to the analyte of interest the sensor platform can be used for biological or chemical sensing. U.S. Pat. No. 6,688, 162, issued 10 Feb. 2004 to Bachas, et al. provides basic technological background discussion concerning the operation of resonator-type sensor elements in connection with direct quantitative measurement of parameters and characteristics of an analyte of interest (in that case, especially one in the form of a thin film/layer atop a surface of the element). As already mentioned, U.S. Pat. No. 7,113,876 filed 8 Sept. 2004 was granted to three co-applicants hereof (Drs. K. Zeng, K. G. Ong, and C. A. Grimes) as titled "Technique and Electronic Circuitry for Quantifying a Transient Signal using Threshold-crossing Counting to Track Signal Amplitude." Other patents and published manuscripts that share at least one applicant hereof describe applications of resonator-type sensing elements in sensing an environment, itself, and/or the presence, concentration, chemical make up, and so on, of an analyte of interest (e.g., toxins or other undesirable chemical or substance, etc.), include: U.S. Pat. No. 6,639,402 issued 28 Oct. 2003 to Grimes et al. entitled "Temperature, Stress, and Corrosive Sensing Apparatus Utilizing Harmonic Response of Magnetically Soft Sensor Element(s);" U.S. Pat. No. 6,393, 921 B1 issued 28 May 2002 to Grimes et al. entitled "Magnetoelastic Sensing Apparatus and Method for Remote Pressure Query of an Environment," U.S. Pat. No. 6,397,661 B1 issued 4 Jun. 2002 to Grimes et al. entitled "Remote Magnetoelastic Analyte, Viscosity and Temperature Sensing Apparatus and Associated Method of Sensing," Grimes, C. A., K. G. Ong, et al. "Magnetoelastic sensors for remote query environmental monitoring," Journal of Smart Materials and Structures, vol. 8 (1999) 639-646; K. Zeng, K. G. Ong, C. Mungle, and C. A. Grimes, Rev. Sci. Instruments Vol. 73, 4375-4380 (December 2002) (wherein a unique frequency counting technique was reported to determine resonance frequency of a sensor by counting, after termination of the excitation signal, the zero-crossings of the transitory ring-down oscillation, damping was not addressed); and Jain, M. K., C. A. Grimes, "*A Wireless Magnetoelastic Micro-Sensor Array for Simultaneous Measurement of Temperature and Pressure*," IEEE Transactions on Magnetics, vol. 37, No. 4, pp. 2022-2024, 2001.

III. Digital computers. A processor is the set of logic devices/circuitry that responds to and processes instructions to drive a computerized device. The central processing unit (CPU) is considered the computing part of a digital or other type of computerized system. Often referred to simply as a processor, a CPU is made up of the control unit, program sequencer, and an arithmetic logic unit (ALU)—a high-speed circuit that does calculating and comparing. Numbers are transferred from memory into the ALU for calculation, and the results are sent back into memory. Alphanumeric data is sent from memory into the ALU for comparing. The CPUs of a computer may be contained on a single 'chip', often referred to as microprocessors because of their tiny physical size. As is well known, the basic elements of a simple computer include a CPU, clock and main memory; whereas a complete computer system requires the addition of control units, input, output and storage devices, as well as an operating system. The tiny devices referred to as 'microprocessors' typically contain the processing components of a CPU as integrated circuitry, along with associated bus interface. A microcontroller typically incorporates one or more microprocessor, memory, and I/O circuits as an integrated circuit (IC). Computer instruction(s) are used to trigger computations carried out by the CPU. Frequency counters are digital indicating meters for measurement and display of input signals in the form of square wave(s) and pulse(s). Binary counters are digital circuits that have a clock input and one or more count output; the count output may give the number of clock cycles for a clock input, or may be employed to count pulses for an input digital waveform.

IV. Microelectronics—Structures and Devices. Microelectronics is that area of electronics technology associated with the fabrication of electronic systems or subsystems using extremely small (microcircuit-level) components. Chip, microchip, integrated circuit (IC), often used interchangeably, generally refer to any one or interrelated operational set of micro-miniaturized, electronic circuits, or microdevices—including microprocessors—that have been designed for use as electrical components, processors, computer memory, as well as countless other special purpose.

V. Computer Memory and Computer Readable Storage. While the word 'memory' has historically referred to that which is stored temporarily, with storage traditionally used to refer to a semi-permanent or permanent holding place for digital data—such as that entered by a user for holding long term—more-recently, the definitions of these terms have blurred. A non-exhaustive listing of well known computer readable storage device technologies are categorized here for reference: (1) magetic tape technologies; (2) magnetic disk technologies include floppy disk/diskettes, fixed hard disks (often in desktops, laptops, workstations, etc.), (3) solid-state disk (SSD) technology including DRAM and 'flash memory'; and (4) optical disk technology, including magneto-optical disks, PD, CD-ROM, CD-R, CD-RW, DVD-ROM, DVD-R, DVD-RAM, WORM, OROM, holographic, solid state optical disk technology, and so on.

VI. Electromagnetic waves. It is well known that electric and magnetic fields are fundamentally fields of force that originate from electric charges. Whether a force field may be termed electric, magnetic, or electromagnetic (EM) hinges on the motional state of the electric charges relative to the point at which field observations are made. Electric charges at rest relative to an observation point give rise to an electrostatic (time-independent) field there. The relative motion of the charges provides an additional force field called magnetic. That added field is magnetostatic if the charges are moving at constant velocities relative to the observation point. Accelerated motion of charges produces both time-varying electric and magnetic fields, or electromagnetic fields. Exposure of a time-varying, typically sinusoidal magnetic field will induce an associated time-varying current ('alternating current' or 'ac'/'AC') in a ferromagnetic sample such that it will emit EM energy.

SUMMARY OF THE INVENTION

It is a primary object to provide a technique and associated circuitry and program code, for characterizing the response of a magnetoelastic sensor element during exposure to an excitation field generated by an interrogation coil. The circuitry includes: (a) an excitation circuit for providing an AC excitation signal to the coil; (b) a receive circuit for measuring a total sensor signal from the coil with the sensor element positioned within the excitation field; (c) a phase detection circuit for detecting phase of said total sensor signal so measured; and (d) a processing unit for determining: (i) a total measured impedance spectrum from the measured total sensor signal, and (ii) a plurality of magnitude values representing the real part of a reconstructed impedance spectrum for the sensor element. Additionally a digital synthesis circuitry is used to aid in providing the AC excitation signal. The AC excitation signal is provided in conjunction with measuring a total sensor signal in a manner that includes: (i) performing a frequency sweep over a selected range of frequencies, and (ii) for each of a plurality of consecutive frequencies within the selected range, measuring a coil voltage magnitude and phase across the coil and applying the expression $Z_t(\omega)=V(\omega)/I(\omega)$ wherein $I(\omega)$ represents said AC excitation signal as a current applied to the coil, $V(\omega)$ represents a voltage measured across the coil with the sensor element positioned within the excitation field, and $Z_t(\omega)$ represents said total measured impedance. A relative maximum of the plurality of magnitude values so determined for the reconstructed impedance spectrum represents the response at a resonance frequency of the sensor element. The circuitry, in operation, is used for sensing to obtain information about an environment within which the sensor element is immersed as positioned within the excitation field.

The many distinguishing features set forth herein provide further unique capabilities to the core combination of features of the circuitry and associated method/technique for characterizing the response of a magnetoelastic sensor element during exposure to an excitation field generated by an interrogation coil. The reconstructed impedance spectrum is preferably calculated by subtracting an impedance attributable to the coil during the time an AC excitation signal is provided, from the total measured impedance. At resonance, this reconstructed impedance spectrum can be calculated by subtracting a real resistance of the impedance attributable to the coil from a real part of the total measured impedance, and subtracting an imaginary reactance of the impedance attributable to the coil from an imaginary part of the total measured impedance. DC biasing circuitry in communication with the coil provides a DC biasing field to which the sensor element is also exposed; the sensor element is preferably positioned within the excitation field within a spacing created by a winding of the interrogation coil. A phase detection circuit preferably includes circuitry for generating a reference signal against which the phase of the total sensor signal is compared to find a phase difference there-between.

In a related aspect, also disclosed is a method and associated program code for characterizing the response of a magnetoelastic sensor element during exposure to an excitation field generated by an interrogation coil. The method includes: (a) providing an AC excitation signal to the coil; (b) measuring a total sensor signal from the coil with the sensor element positioned within the excitation field within a spacing created by a winding of the coil; (c) detecting the phase of the total sensor signal so measured; and (d) automatically determining: (i) a total measured impedance spectrum from the total sensor signal so measured, and (ii) a plurality of magnitude values representing the real part of a reconstructed impedance spectrum for the sensor element. A suitable processing unit can be used, and incorporated into a microcontroller or microprocessor for calculations and determining various characteristics, as explained.

One will appreciate the distinguishable features of the circuitry and associated technique described herein from those of known telemetry techniques, including prior designs invented by one or a collection of the applicants hereof. Certain of the unique features, and further unique combinations of features—as supported and contemplated—may provide one or more of a variety of advantages, among which include: (a) system integration flexibility/versatility; (b) ongoing, reliable monitoring/investigation without disruption of the environment undergoing investigation; and (c) handy integration into equipment/systems currently in use to 'sense' or investigate one or more environments, or some component or constituent thereof (e.g., an analyte of interest).

BRIEF DESCRIPTION OF THE DRAWINGS

FIG. 25 A graphical representation of the measured blood coagulation curve using the impedance analysis technique of the invention: The signal amplitude was normalized to the maximum amplitude.

FIG. 26 Illustration depicting model sensor response to a sinusoidal pulse excitation. The sensor response includes a "forced response" and a "free response."

FIG. 27 A high-level block diagram depicting a system 200 of circuit elements (core as well as additional elements) for automatic implementation of the unique impedance analysis technique of the invention. Please refer also to FIG. 7.

DETAILED DESCRIPTION OF EMBODIMENTS DEPICTED IN THE DRAWINGS

Occasional reference will be made back-and-forth to each of the figures so as to better appreciate the features of the new circuitry, its components/subcomponents, and associated method of the invention depicted throughout—as well as to incorporate examples of employing the unique circuitry and method of the invention, in sensing platforms. The examples provided herein showcase the use of magetoelastic sensor elements—preferably at least somewhat elongated in shape—as they emit responses from which useful information about an environment, analyte or sample of interest may be gained, during ac excitation.

Figure 1:
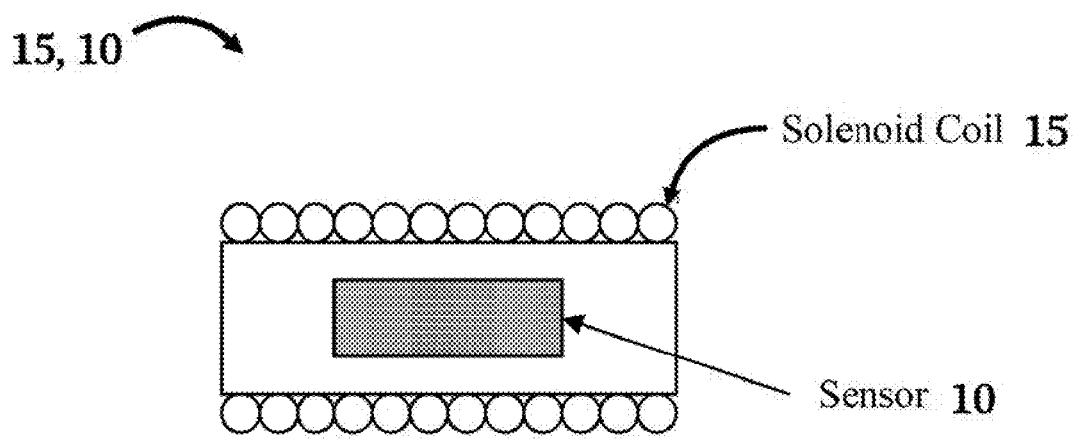
FIG. 1 A high-level schematic generally illustrating position of a solenoid coil winding 15 and a sensor element 10 located inside the winding; the elongated sensor shape has a length shown parallel to an axis of the coil.
Figure 2:
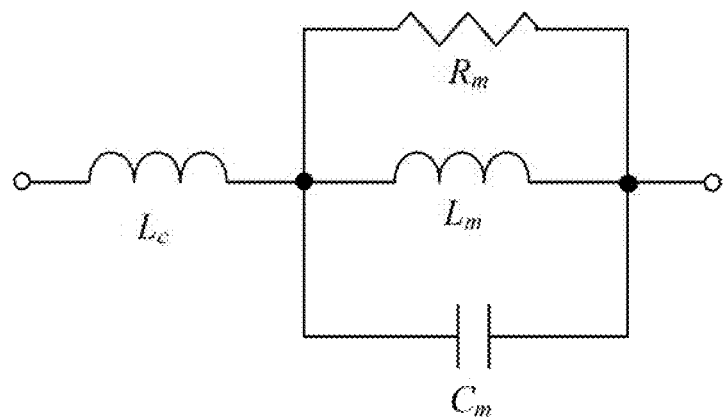
FIG. 2 An equivalent circuit model (circuit diagram) of a system consisting of magnetoelastic sensor and coil: $L_m$, $C_m$, and $G_m$ form a parallel LC oscillation circuit representing the vibrating sensor, wherein subscript "m" indicates the inductance, capacitance, and conductance induced by motion and $L_c$ represents static inductance of the coil.

As illustrated in FIG. 1, an elongated magnetoelastic sensor element 10 is shown in proximity to solenoid coil 15—placed within the volume, or spacing, created by an inner diameter of—with its length parallel to the coil axis. While only one element is depicted, more may be included, each constructed/shaped and tuned to provide a variety of different types of information about the environment/analyte of interest within which the sensor elements are immersed for sensing. The sensor unit comprising coil 15 and one or more sensor element 10 is also referred to occasionally as 15/10. When an ac (alternatively, "AC") excitation signal is applied to the coil 15, a time varying magnetic field is generated inside the coil, thus causing the sensor to vibrate, with the vibration amplitude and phase being functions of (i.e., mathematically related to) the excitation frequency and coil impedance. The sensor element vibration, in turn, generates a magnetic flux that induces an ac voltage across the coil. The vibration-induced voltage is superimposed on the excitation signal, thus changing the effective impedance of the coil unit 'as seen' by the excitation signal source. As uniquely recognized by the applicants hereof, the vibrating sensor is modeled as an RLC parallel oscillation circuit and the coil as an ideal inductor in series with the sensor oscillation circuit—shown in FIG. 2—where $L_m$, $C_m$, and $R_m$ respectively represent the inductance, capacitance, and resistance induced by motion (sensor vibration), and $L_c$ represents the static inductance of the coil when there is no sensor vibration. Thus, total impedance $Z_t(\omega)$ of the equivalent circuit—namely, the coil combined with the vibrating sensor—can be represented by the expression:

$$Z_t(\omega) = j\omega L_c + \frac{1}{1/R_m + j\omega C_m + 1/j\omega L_m} \quad \text{Equation (4)}$$

where $\omega$ is the angular frequency. The impedance is a complex value that can be expressed in terms of a magnitude, $|Z_t(\omega)|$, and a phase, $\phi_t(\omega)$, given by $$Z_t(\omega) = |Z_t(\omega)|\exp[j\phi_t(\omega)] \quad \text{Equation (5)}$$

where $$|Z_t(\omega)| = \left(\frac{\omega_a}{\omega_0}\right)^2 \cdot \frac{\left((1-(\omega/\omega_a)^2)^2 + (2\zeta_a(\omega/\omega_a))^2\right)^{1/2}}{\left((1-(\omega/\omega_0)^2)^2 + (2\zeta_0(\omega/\omega_0))^2\right)^{1/2}} \quad \text{Equation (6)}$$

$$\phi_t(\omega) = \tan^{-1}\frac{2\zeta_n\omega/\omega_0}{1-(\omega/\omega_0)^2} - \tan^{-1}\frac{2\zeta_a\omega/\omega_a}{1-(\omega/\omega_a)^2} \quad \text{Equation (7)}$$

$$\omega_0 = \sqrt{\frac{1}{L_m C_m}}, \quad \omega_a = \sqrt{\frac{1}{L'_m C_m}}, \quad \zeta_0 = \frac{R_m}{2}\sqrt{\frac{L_m}{C_m}},$$

$$\zeta_a = \frac{R_m}{2}\sqrt{\frac{L_m}{C'_m}}, \quad L'_m = \frac{L_c L_m}{L_c + L_m}$$

$\omega_0$ is the resonance (parallel resonance of $L_m$ and $C_m$) frequency and $\zeta_0$ is the resonance damping factor, both independent of the coil inductance. $\omega_a$ is the anti-resonance (series resonance of $L_m'$ and $C_m$) frequency and $\zeta_a$ is the anti-resonance damping factor, both dependent upon the coil inductance. Mathematical manipulation of the impedance as a function of $\omega_0$, $\omega_a$, $\zeta_0$, and $\zeta_a$ is done so as to represent the impedance because the parameters $\omega_0$, $\omega_a$, $\zeta_0$, and $\zeta_a$ are handily measured using the measurement instrumentation described herein. It should be noted that since preferably as the system is contemplated herein $L_m > L_m'$, it follows that $\zeta_0 > \zeta_a$ and $\omega_0 > \omega_a$.

When a constant ac current $I(\omega)$ is applied to the coil and voltage $V(\omega)$ is measured across the coil, total impedance $Z_t(\omega)$ can be expressed as $$Z_t(\omega) = V(\omega)/I(\omega) \quad \text{Equation (8)}$$

Figure 7:
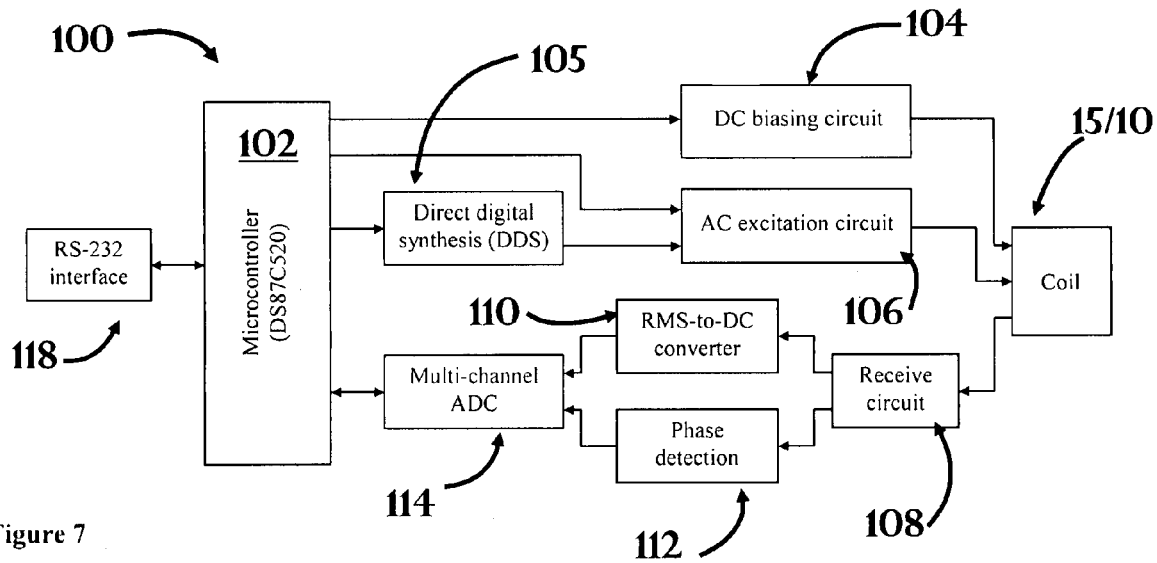
FIG. 7 A high-level block diagram depicting a system 100 of circuit elements (core as well as additional elements) for automatic implementation of the unique impedance analysis technique of the invention.
Figure 12:
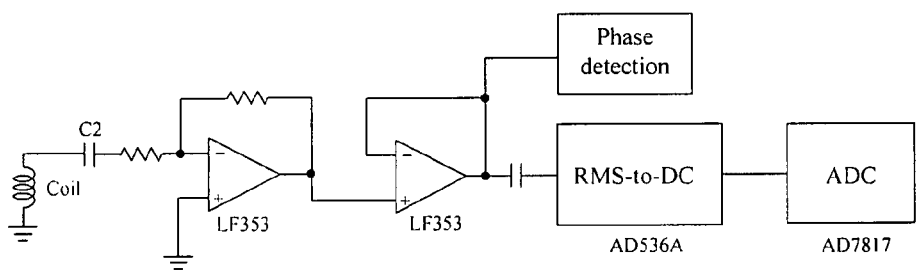
FIG. 12 Circuit diagram detailing receive circuitry 108' (108, FIG. 7), by way of example here to include an op-amp with a voltage gain of 20 for amplification of sensor signal received from coil unit (15/10, FIG. 1) during operation.

As used throughout 'measured' impedance refers to the total impedance of the coil 15 combined with the sensor element 10, as measured by receiving circuitry (see, also, FIGS. 7, 12, and 26). Uniquely recognized by applicants in this context—to gain useful information from magnetoelastic resonant sensor element(s) about an environment, analyte/sample of interest—preferably, the coil's impedance is subtracted from the total impedance to obtain the sensor element's impedance. As mentioned above, the impedance is a complex value (since the system is driven by an ac excitation signal), see equation (4). Therefore, simple subtraction is not enough to accomplish a removal of the coil's impedance effect(s) (i.e., impedance attributable to coil) from the measured impedance of the unit 15/10. As uniquely applied here, the total complex impedance is first expressed in terms of a real (resistance), $Re[Z_t(\omega)]$, and an imaginary (reactance), $Im[Z_t(\omega)]$, using the following $$Z_t(\omega) = Re[Z_t(\omega)] + j\, Im[Z_t(\omega)] \quad \text{Equation (9)}$$

where $$Re[Z_t(\omega)] = |Z_t(\omega)|\cos[\phi_t(\omega)] \quad \text{Equation (10)}$$

and $$Im[Z_t(\omega)] = |Z_t(\omega)|\sin[\phi_t(\omega)] \quad \text{Equation (11)}$$

Subtraction of coil impedance from total complex impedance is accomplished by separate subtraction of the real part and of the imaginary part, which is represented as follows $$Re[Z_s(\omega)] = Re[Z_t(\omega)] - Re[Z_c(\omega)] \quad \text{Equation (12)}$$

and $$Im[Z_s(\omega)] = Im[Z_t(\omega)] - Im[Z_c(\omega)] \quad \text{Equation (13)}$$

where the subscript "s" indicates sensor element impedance and "c" indicates the coil impedance.

At the resonance frequency, $$\omega_0 = \sqrt{\frac{1}{L_m C_m}},$$

the sensor inductance and capacitance cancel each other $$\left(\omega_0 L_m = \frac{1}{\omega_0 C_m}\right),$$

such that the imaginary part of the total impedance is completely attributed to the coil inductance, this can be mathematically expressed by the following $$Im[Z_t(\omega_0)] = Im[Z_c(\omega_0)] = \omega_0 L_c \qquad \text{Equation (14)}$$

At all frequencies, the reactance of the sensor is calculated by $$Im[Z_s(\omega)] = Im[Z_t(\omega)] - \omega L_c = Im[Z_t(\omega)] - Im[Z_t(\omega_0)] \cdot (\omega/\omega_0) \qquad \text{Equation (15)}$$

Also uniquely recognized, at the resonance frequency $$\omega_0 = \sqrt{\frac{1}{L_m C_m}},$$

the real (resistance) of the sensor element is at a maximum, $Re[Z_s(\omega_0)] = Re[Z_t(\omega_0)] = R_m$. Therefore, the resonance frequency can be determined by locating the peak value of the real part of the total impedance. As mentioned above, $\omega_0$ represents the resonance (parallel resonance of $L_m$ and $C_m$) frequency, which is independent of the coil inductance. After subtracting the coil impedance, the 'pure' sensor impedance (i.e., impedance attributable to sensor element) is reconstructed as $$|Z_s(\omega)| = (Re[Z_s(\omega)]^2 + Im[Z_s(\omega)]^2)^{1/2} \qquad \text{Equation (16)}$$

$$\phi_s(\omega) = \tan^{-1}\left(\frac{Im[Z_s(\omega)]}{Re[Z_s(\omega)]}\right) \qquad \text{Equation (17)}$$

Figure 3:
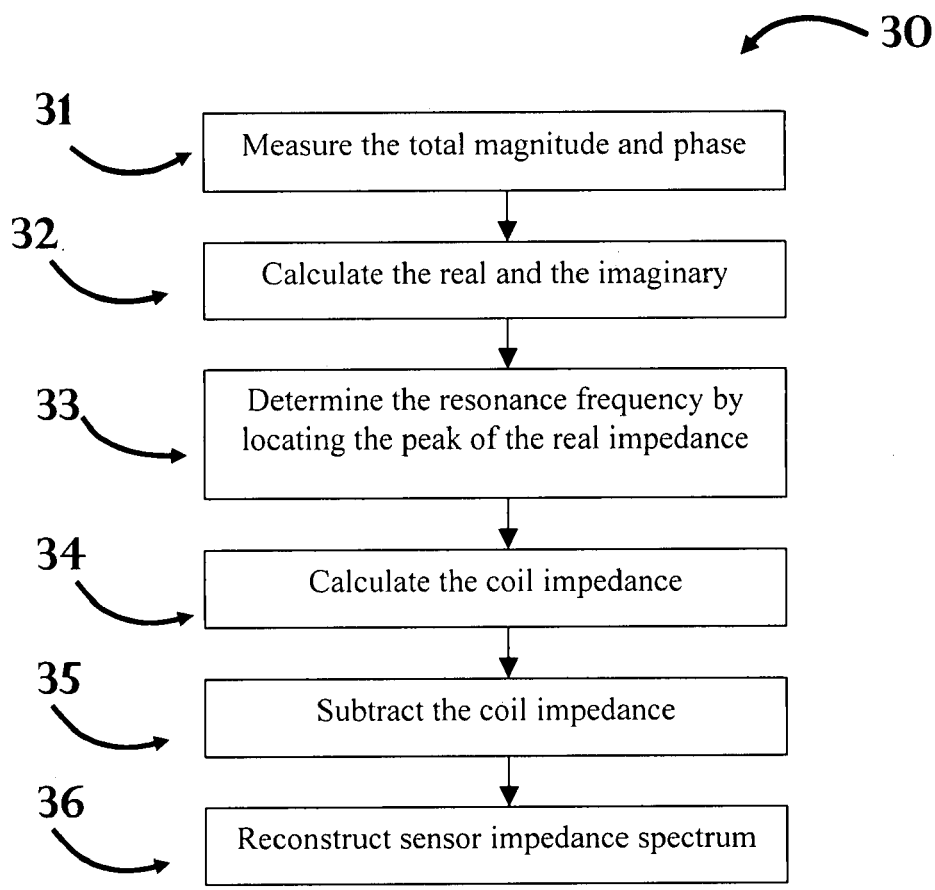
FIG. 3 A flow diagram depicting a method 30 of reconstructing the sensor impedance spectrum by subtracting the coil impedance from a total measured impedance.
Figure 4:
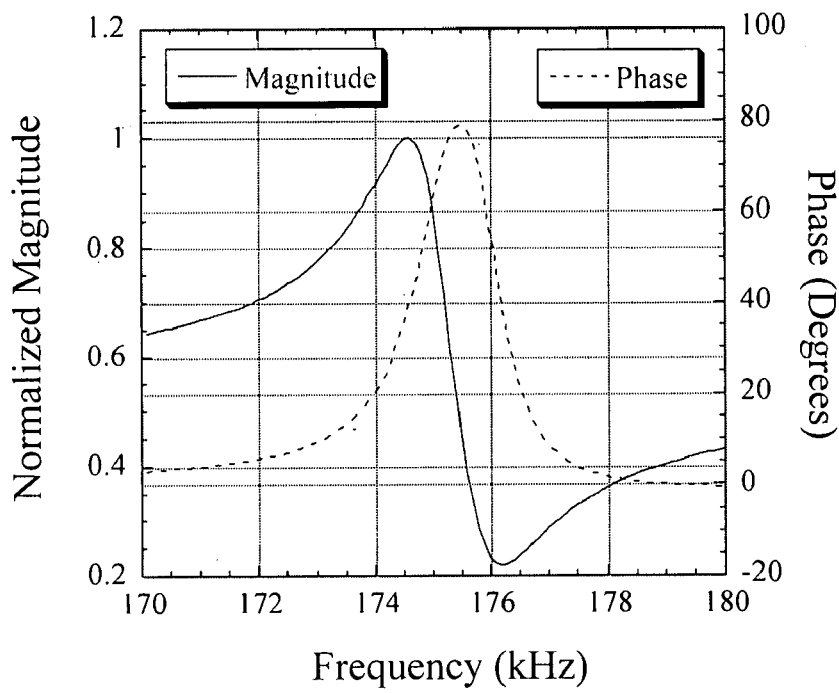
FIG. 4 A graphical representation of the impedance spectrum (magnitude and phase) of the equivalent circuit model (FIG. 2). The magnitude has a peak due to sensor resonance and a valley due to anti-resonance caused by coil inductance.
Figure 5:
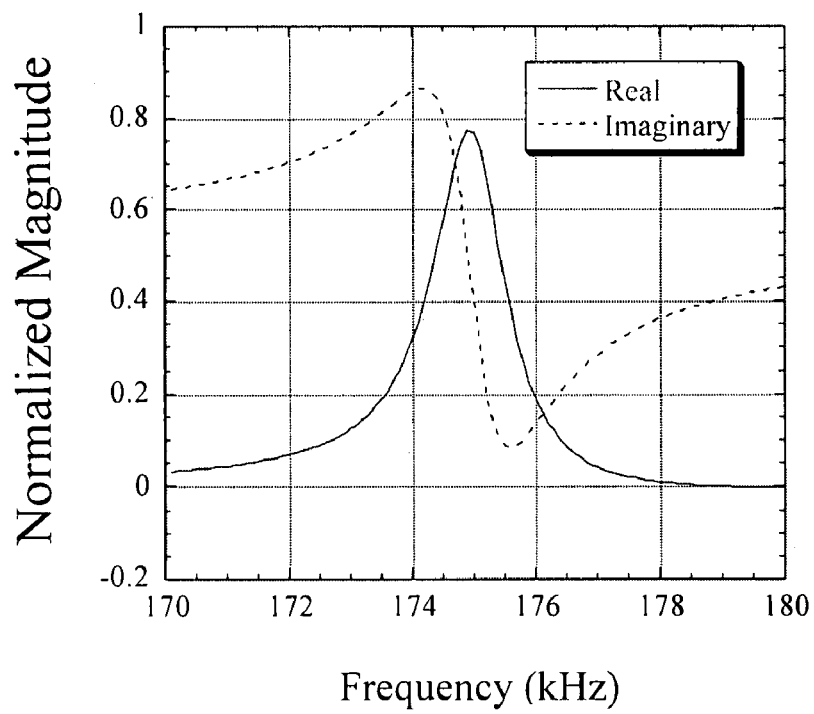
FIG. 5 A graphical representation of the real and imaginary parts of an impedance spectrum (i.e., magnitude as a function of frequency) of the equivalent circuit model (FIG. 2).
Figure 6:
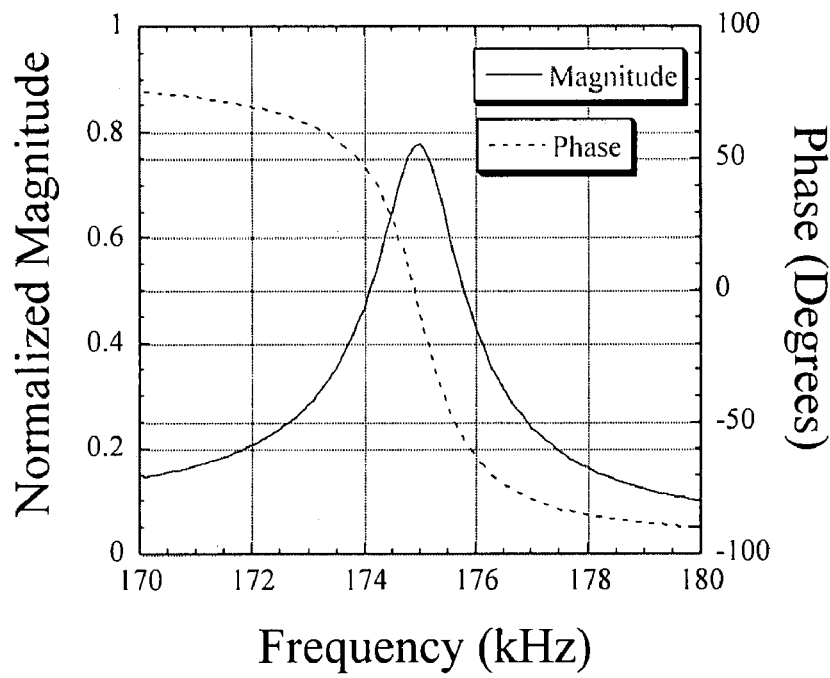
FIG. 6 A graphical representation of the reconstructed impedance spectrum of the sensor element after subtracting the coil impedance from total impedance of a coil combined with sensor element for the equivalent circuit model (FIG. 2).

FIG. 3 is a flow diagram illustrating core and further distinguishing features of the new technique 30 for sensor impedance reconstruction, according to the invention. This diagram highlights steps, in summary format, of features detailed elsewhere, herein: Measure a magnitude and phase of the total signal from the sensor-coil unit (whether one or more sensor elements are within the coil) 31 for which a real part and imaginary part are calculated 32 (real and imaginary parts of impedance spectrum plotted in FIG. 5 for equivalent circuit model), the real part that a relative max (peak) of the real impedance as identified 33 occurs at resonance for the unit. Calculate and subtract 34, 35 the impedance attributable to the coil, from the total signal measured, collectively, for the sensor-coil unit, to reconstruct a sensor impedance spectrum 36 that characterizes the response of the sensor element(s), see the plots in FIGS. 6 and 19 graphically depicting examples of a 'reconstructed' impedance spectrum. Plugging empirical values of the parameters $\omega_0$, $\omega_a$, $\zeta_0$, and $\zeta_a$ into equations (6) and (7) to obtain the impedance spectrum, magnitude and phase, of a specific sensor. For example, for a magnetoelastic sensor of 12.7 mm×6 mm×28 μm, we can use $\omega_0 = 2\pi \cdot 175$ (kHz), $\omega_a = 2\pi \cdot 176$ (kHz), $\zeta_0 = 0.004$, and $\zeta_a = 0.003$. FIG. 4 depicts plots of magnitude (normalized to the maximum magnitude) and the phase versus frequency from 170 kHz to 180 kHz. In the magnitude plot, one will note a peak due to the resonance (parallel resonance) of the sensor and a valley due to the anti-resonance (series resonance) caused by the coil inductance. The real and imaginary parts of the impedance spectrum are calculated using Equations (10) and (11); these are graphed in FIG. 5. There is a peak in the real part, corresponding to a net reactance attributed to the coil inductance, located at the resonance frequency $\omega_0 = 2\pi \cdot 175$ (kHz). The coil impedance is subtracted, as explained above, from the total impedance using Equation (15). After the subtraction, the pure sensor impedance spectrum is reconstructed using Equations (16) and (17); the results are shown in FIG. 6 as labeled separate plots—one for magnitude using Equation (16) the other for phase using Equation (17). The reconstructed impedance spectrum characterizes the sensor behavior. The resonance frequency is determined by locating the peak value of the real part of impedance or the magnitude; and the Q factor is determined from the magnitude by $$Q = \frac{\omega_0}{\Delta \omega} \qquad \text{Equation (19)}$$

where $\Delta\omega$ is the half-power point bandwidth.

EXAMPLE 01

An Electronic Implementation

FIG. 7 is a circuit block diagram of one preferred electronic implementation 100 of the impedance analysis technique for characterizing magnetoelastic sensors. The identified functional blocks in FIG. 7 of one alternative preferred system, may include the following:

Microcontroller/microprocessor (102, FIG. 7): The microcontroller used in this example circuit is a DS87C520 high-speed microcontroller from Dallas Semiconductor Corporation. The DS87C520 microcontroller belongs to the 8052 microcontroller family. This device is promoted as having efficient bit manipulation, easy I/O interface, and large on-chip memory (16 KB of ROM and 1 KB of MOVX RAM). The DS87C520 can work up to 33 MHz. In the circuit, a 20 MHz crystal clock is used.

RS-232 interface (118, FIG. 7): An RS-232 serial communication interface is designed to enable computerized operation, thus making use of modern computers for signal processing and data storage. The serial port 0 of the microcontroller is used for the RS-232 interface, and the Timer 2 of the microcontroller is used to provide a baud rate of 9600.

Direct digital synthesis (DDS) (105, FIG. 7): The circuit utilizes a direct digital synthesis (DDS) technique that digitally synthesizes highly pure sine wave of numerically controlled frequency from a reference clock. The DDS chip, AD9832 from Analog Devices, is serially interfaced with the microcontroller; its 32-bit frequency control word enables sub-hertz frequency resolution. In the circuit, the DDS chip shares the crystal clock, 20 MHz, with the DS87C520 microcontroller, and the frequency resolution of the synthesized sine wave is 0.04 Hz.

Multi-channel ADC (114, FIG. 7): For analog-to-digital (A/D) conversion, a four channel 10-bit ADC chip, AD7817 from Analog Devices, is serially interfaced with the microcontroller to digitize both magnitude and phase of the sensor signal. When referenced to a voltage of 2.5 volts, the AD7817 has a voltage measurement resolution of about 2.5 mV.

RMS-to-DC converter (110, FIG. 7): For voltage magnitude measurement, an RMS-to-DC converter, AD536A from Analog Devices, is used. The AD536A is a complete integrated circuit that directly computes the true root-mean-square (RMS) value of an ac signal. The AD536A requires only one external capacitor to perform the RMS-to-DC conversion, with a bandwidth of 450 kHz.

Figure 8:
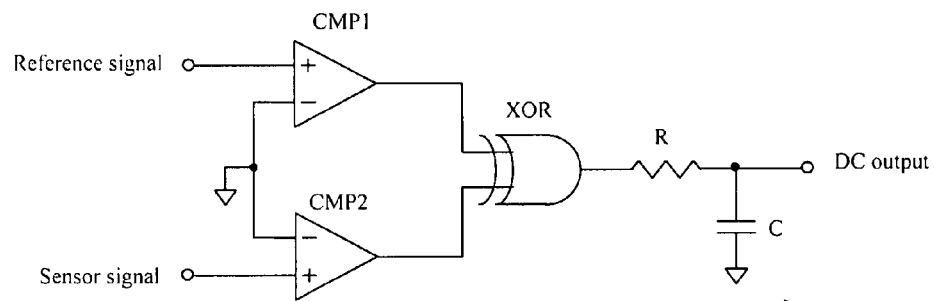
FIG. 8 Circuit diagram of a collection elements for phase detection 112' (112, FIG. 7), by way of example here, using an exclusive OR (XOR) gate: Phase detection circuitry converts the phase difference between the sensor signal and the reference signal into a proportional dc voltage level.
Figure 9:
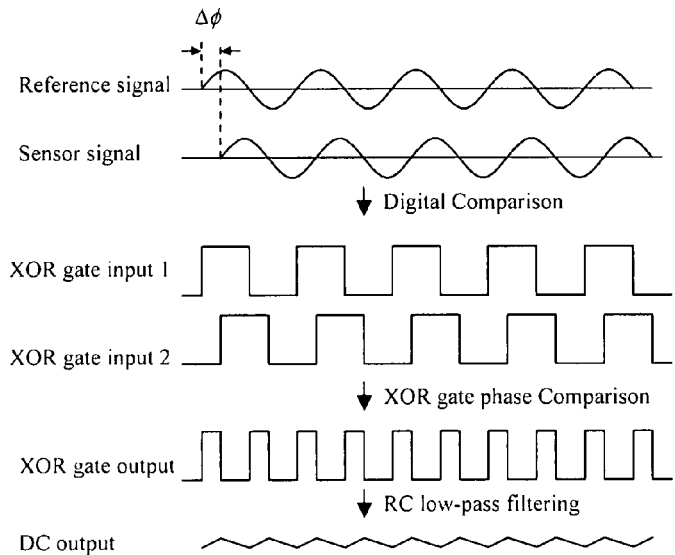
FIG. 9 A schematic graphically depicting phase detection: achieved, here, by comparing the sensor signal to a reference signal that has the same frequency as the sensor signal.

Phase detection (112, FIG. 7): A phase detection circuit, as shown in FIG. 8, is designed to measure the phase of the received sensor signal. FIG. 9 illustrates the phase detection procedure. Both the reference signal and the sensor signal are first fed to two comparators, with the two resulting 50% duty cycle square waves fed to the two inputs of the XOR gate. The output of the XOR gate is a square wave with a duty cycle proportional to the phase difference $\Delta\phi$ between the sensor signal and reference signal. Following the XOR gate is an RC low pass filter, which outputs a dc voltage proportional to the duty cycle and hence the phase difference.

Figure 10:
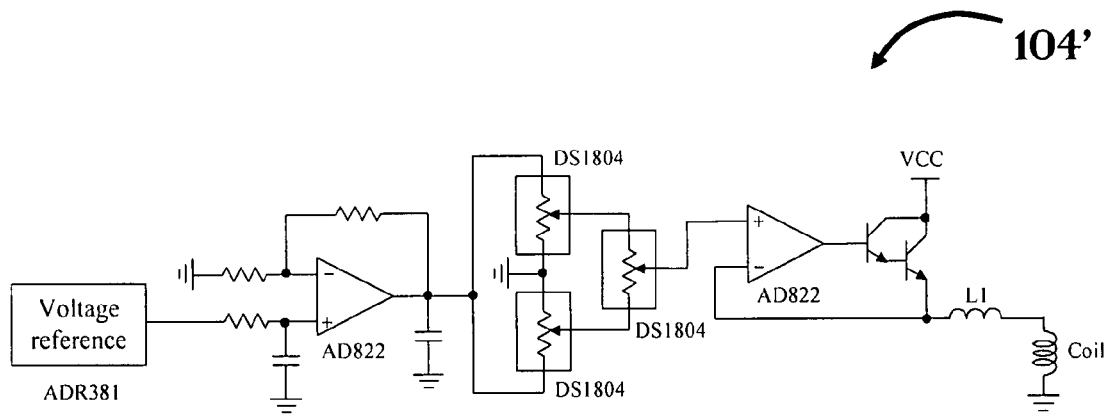
FIG. 10 Circuit diagram of a collection of elements 104' for dc biasing (104, FIG. 7) providing a tunable dc voltage to coil 15 for biasing the sensor element(s) 10.

DC biasing circuit (104, FIG. 7): The dc biasing circuit provides a tunable dc voltage to the coil to generate a dc biasing magnetic field that aligns the randomly oriented magnetic domains in the sensor, facilitating sensor excitation and detection. FIG. 10 shows the detailed circuit design. A precision band gap voltage reference, ADR381 from Analog Devices, is used to provide an accurate voltage source of 2.5 V. Three digital potentiometers, DS1804 from Dallas Semiconductor Corporation, are used in combination to digitally tune the voltage for optimal dc biasing. A large (15 MH) inductor, L1, is used to block the ac signal.

Figure 11:
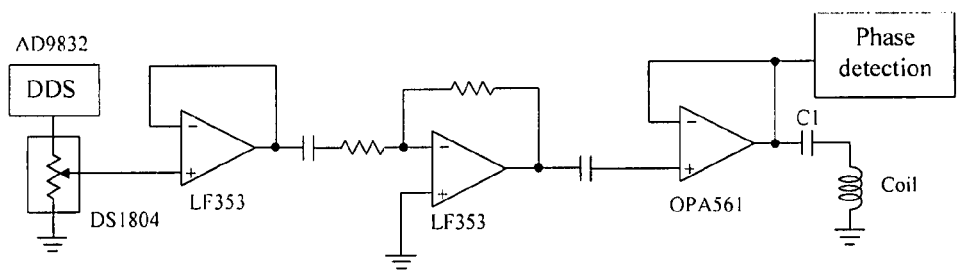
FIG. 11 Circuit diagram of a collection of elements 106' for ac (AC) excitation (106, FIG. 7) providing a tunable ac voltage to coil 15 for sensor element excitation.

AC excitation circuit (106, FIG. 7): An ac excitation circuit is designed to provide a digitally tunable ac signal for sensor excitation, as shown in FIG. 11. A DS1804 digital potentiometer is used to tune the DDS output. The tuned ac signal, followed by a voltage follower, is first amplified by an LF353 op-amp and then boosted by a high current op-amp OPA561. A small capacitor C1, 1000 pF, is used to couple the ac signal to the coil. The excitation signal is also sent to the phase detection circuit as the reference signal for phase comparison.

Receive circuit/circuitry (108, FIG. 7): FIG. 12 shows the receiving circuit/circuitry. A simple inverting amplifier with a voltage gain of 20 is used to amplify the ac signal across the coil. The amplified signal, followed by a voltage follower, is sent to the RMS-to-DC converter and the phase detection circuit for magnitude and phase measurement.

Further Details of Example 01 System Components

Figure 13:
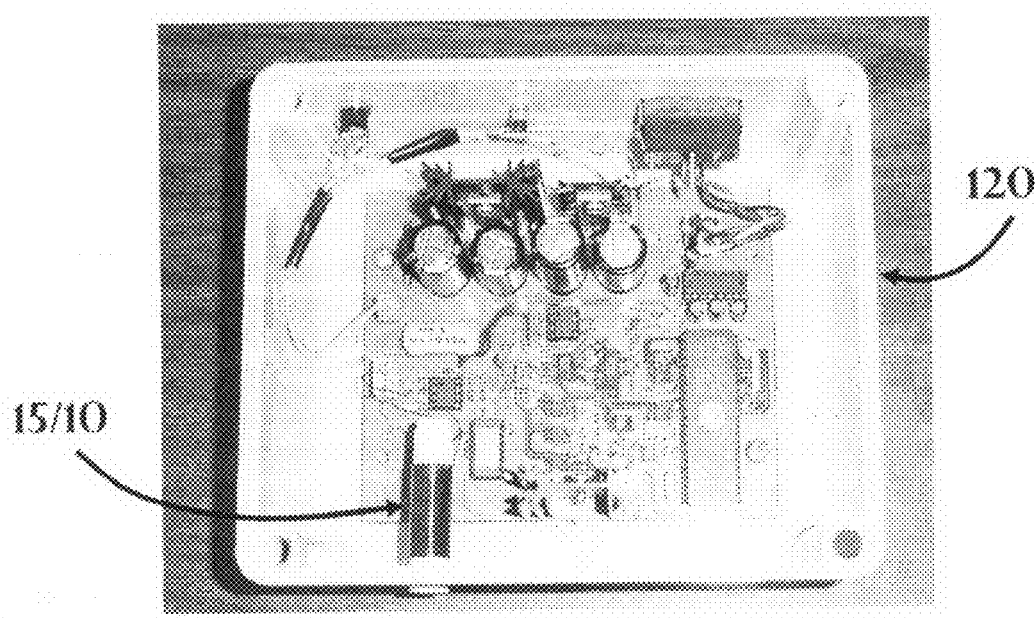
FIG. 13 A top plan view (digital picture) of sensing system circuitry, including solenoid coil 15, packaged into suitable housing 120: By way of example, only, for purposes of reference in connection with exemplary embodiments detailed herein, solenoid coil employed/tested was 30 mm in length and 11 mm in diameter, with 200 turns of windings.

FIG. 13 shows certain components of a fabricated circuit board packaged along with a solenoid coil 15 into a plastic box/housing 120, referred to, occasionally, as "ME box". The solenoid coil shown, here, is 30 mm in length and 11 mm in diameter, with 200 windings using 0.2 mm diameter insulated copper wire. As a demonstration, the ME box 120 was interfaced with a laptop computer via a serial communication port, in a configuration such as that shown in FIG. 14. During a measurement, a microprocessor unit 130 (computerized device, here, depicted is a laptop personal computer) sends a command along with specified parameters to the ME box 120, which executes the command accordingly and sends the measurement data back to the computer for data storage and analysis. A flexible graphical user interface (GUI) 132 is employed, by way of example only, Microsoft® Visual Basic 6.0® (see FIG. 15). The GUI allows the user to digitally specify all the measurement parameters, such as frequency sweep range, frequency sweep step, dc biasing field, and ac excitation field. The GUI also graphically plots the sensor frequency response and displays all the relevant information. The microcontroller may be programmed using MCS-51 assembly language.

Figure 16:
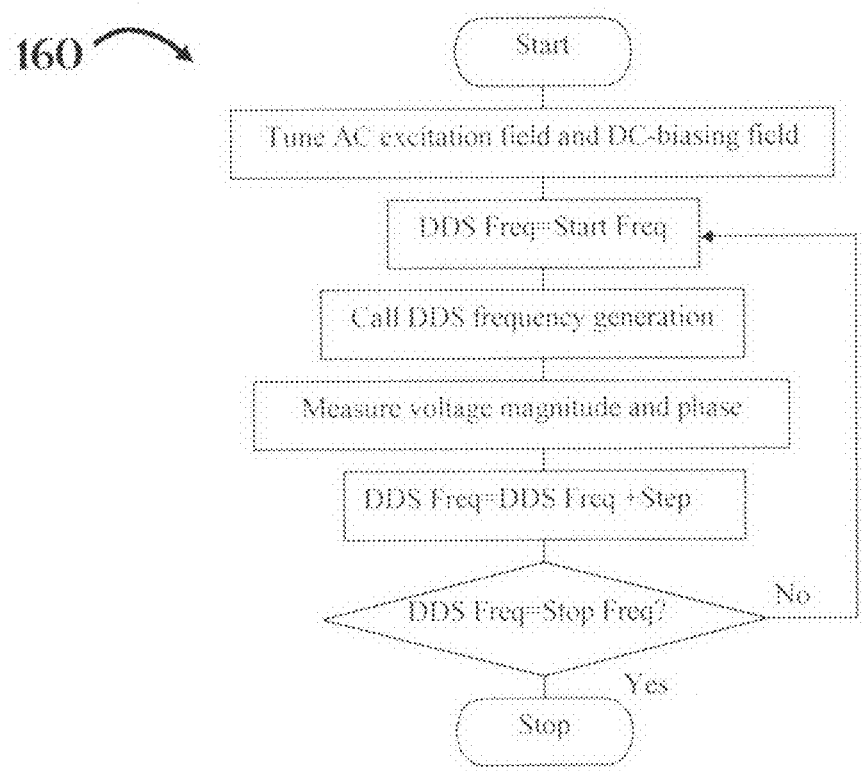
FIG. 16 A flow diagram 160 illustrating a frequency sweep such as is performed by a computerized unit, e.g., microcontroller/microprocessor unit 130, for obtaining measurements from the coil unit 15/10 (coil with sensor element in proximity) in connection with exciting the coil unit 15/10 and collecting measurements for reconstructing an impedance spectrum of one or more sensor element(s).

FIG. 16 is a flowchart summarizing core process step-features of a frequency sweep 160 performed by a computerized unit, such as a microcontroller/microprocessor unit, to obtain an impedance spectrum of a sensor as contemplated. As identified in the boxes: a frequency sweep can start with tuning the ac excitation field and the dc biasing field as specified by the user. Then the microcontroller sets the DDS frequency to the start frequency and measures the sensor response, magnitude and phase, with the measured data stored in the internal memory of the microcontroller. The microcontroller increases the DDS frequency by a specified increment and repeats the measurement until the DDS frequency reaches the specified slop frequency. For each individual frequency—within a sequence of consecutive frequencies of a selected increment—the sensor is measured using 200 averages within a 5 ms period. By way of example, for a frequency range of 20 kHz using a frequency step increment of 100 Hz, a frequency sweep 160 will have 200 discrete data points (whereat a measurement is taken) and will take about one second to perform.

Figure 17:
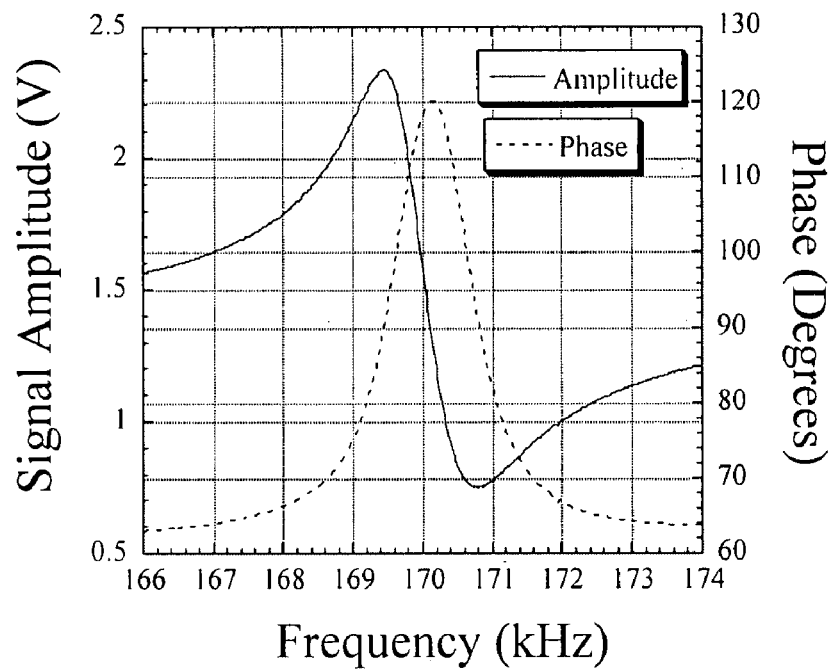
FIG. 17 A graphical representation of the measured frequency response (amplitude and phase) of a 12.7 mm×6 mm×28 μm sensor shear cut from a continuous Metaglas 2826MB ribbon. Compare with the graphical shapes depicted in FIG. 4, which represent an impedance spectrum (magnitude and phase) of the equivalent circuit model of FIG. 2 (where magnitude is shown with a peak due to sensor resonance).
Figure 18:
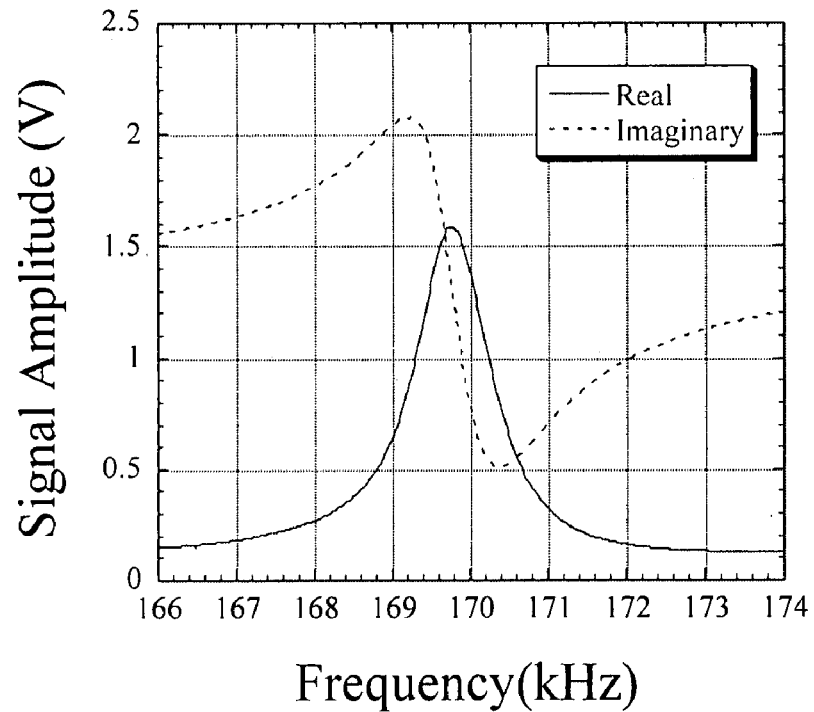
FIG. 18 A graphical representation of the real and imaginary parts of the total frequency response as received/measured having been emitted from the coil sensor unit 15/10. Compare with the graphical shapes depicted in FIG. 5, which represent an impedance spectrum (real and imaginary parts) of the equivalent circuit model of FIG. 2.
Figure 19:
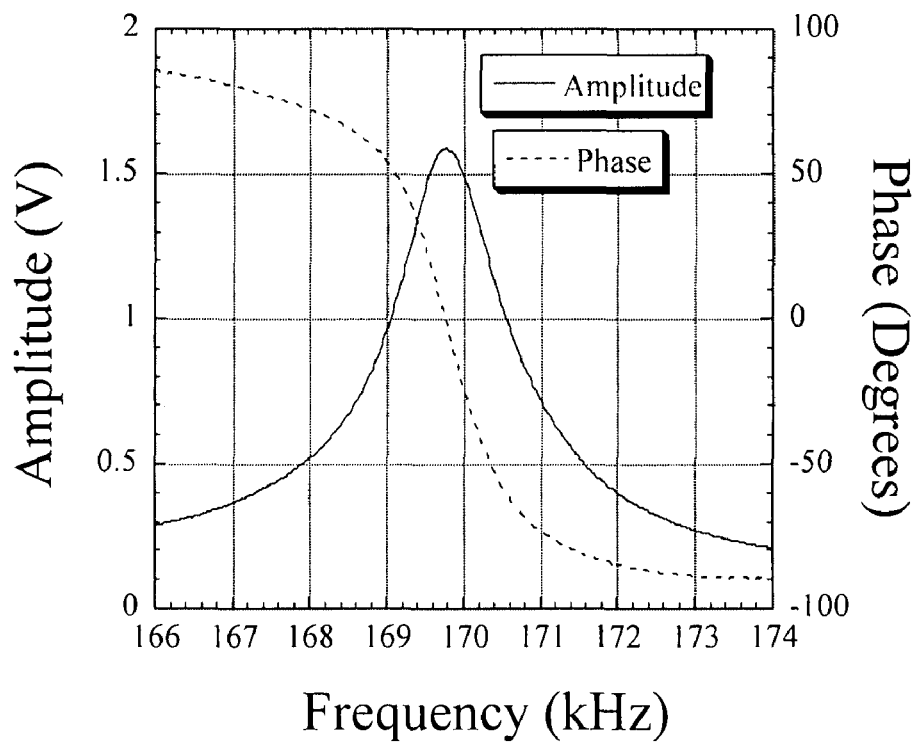
FIG. 19 A graphical representation of the reconstructed frequency response of the sensor obtained by subtracting the coil impedance from the received/measured total impedance of unit 15/10 (coil combined with sensor element). Compare with graphical shapes depicted in FIG. 6, which represent a reconstructed impedance spectrum of the equivalent circuit model of FIG. 2.

In this EXAMPLE 01 system, the response of a sensor element of 12.7 mm×6 mm×28 µm, shear cut from a continuous Metglas 2826MB ribbon, was characterized. The sensor was dc-biased to operate at a resonance frequency of 169.7 kHz. FIG. 17 shows the measured total frequency response (of sensor and coil unit) in terms of amplitude and phase. Note that voltage was not converted into impedance before plotting in FIG. 17, since both voltage and impedance represent the sensor signal to a similar degree/effect. In the measured data, there was a phase offset of about 60 degrees caused by the measurement electronics; this phase offset is calibrated out by programming the microprocessor to do so. After phase calibration, the real and imaginary components, see FIG. 18, are calculated from the amplitude and phase. The coil impedance is then subtracted from the imaginary component as described earlier. It should be noted that due to the finite conductivity of the copper wire the solenoid coil has a small series resistance (about 2 ohms), which is neglected in the equivalent circuit model. The coil resistance is independent of frequency and can be subtracted from the real part of the measured response. The reconstructed sensor response is shown in FIG. 19. Comparing FIGS. 17, 18, and 19 to FIGS. 4, 5, and 6, one can see that measured/experimental results and simulation model (FIG. 2) strongly correlate.

EXAMPLE 02

Example Application #1: Determination of Endotoxin Concentration

The ME box was used for endotoxin detection, where magnetoelastic sensors were used to monitor the gel formation (viscosity change) of the Limulus Amoebocyte Lysate (LAL) assay in response to endotoxin. Magnetoelastic sensors, 12.7 mm×6 mm×28 µm, were immersed in a LAL assay after mixing with test samples of variable endotoxin concentration, and the signal amplitude of the sensor was continuously tracked over time. The results have shown excellent correlation between endotoxin concentration and the maximum clot rate, determined by taking the minimum point of the first derivative of the amplitude-time curve, as well as the clotting-time, defined as the time that corresponds to the maximum clot rate.

In preliminary measurements the LAL assay and endotoxin standard were purchased from Cambrex Biological Science (www.cambrex.com). The LAL assay (PYROGENT Single Test Kit) was a gel-clot assay with sensitivity of 0.06 EU/ml (EU=endotoxin unit). The test kit contained 25 vials of LAL assay in powder form, with each vial calibrated for a test sample of 0.25 ml. The endotoxin standard contained E. coli strain 0111:B4 with concentration of 20 EU per vial. By diluting the endotoxin standard using endotoxin-free glassware and water, also purchased from Cambrex, we prepared a series of test samples with concentrations of 0.0105 EU/ml, 0.0526 EU/ml, 0.132 EU/ml, 0.526 EU/ml, 1.05 EU/ml, 5 EU/ml, and 10 EU/ml; this range of endotoxin concentrations covers those commonly encountered in a medical setting. The magnetoelastic sensors were produced by mechanically shearing a 12.7 mm wide 28 μm thick 2826MB Metglas ribbon into 12.7 mm×6 mm rectangles. The sensors were washed in ethanol, and then rinsed with endotoxin-free water. The sensors were then irradiated under 200 mJ/cm$^2$ UV light for 40 minutes (20 minutes per side) to ensure they were endotoxin free.

Figure 14:
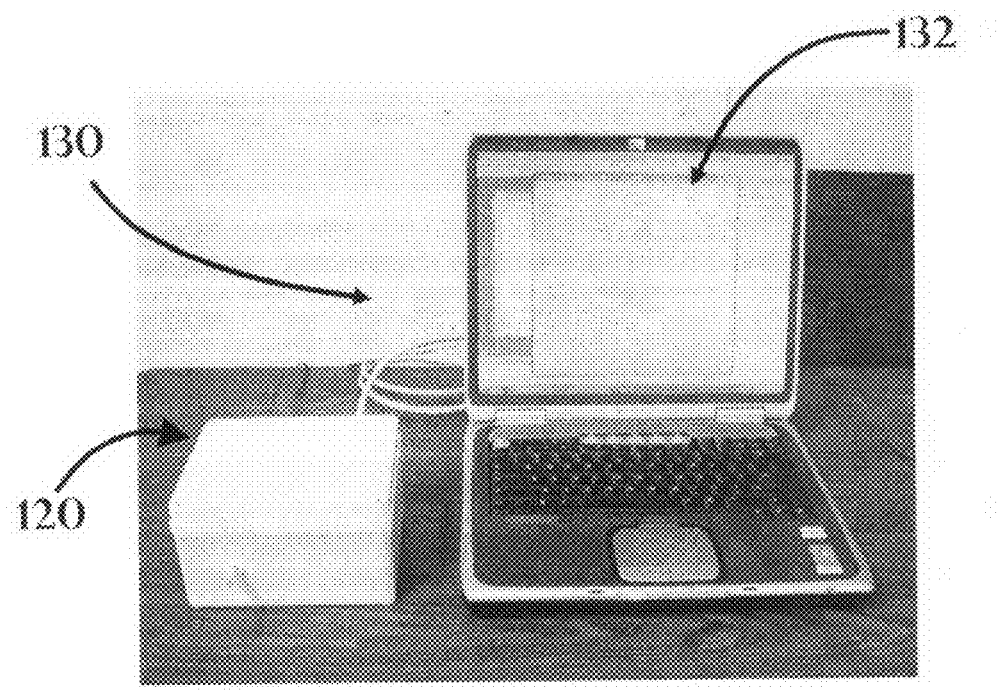
FIG. 14 Isometric (digital picture) of a system including the housing 120 interfaced/in-communication with a laptop-style microprocessor/processing unit 130 for sensor measurement and characterization.
Figure 15:
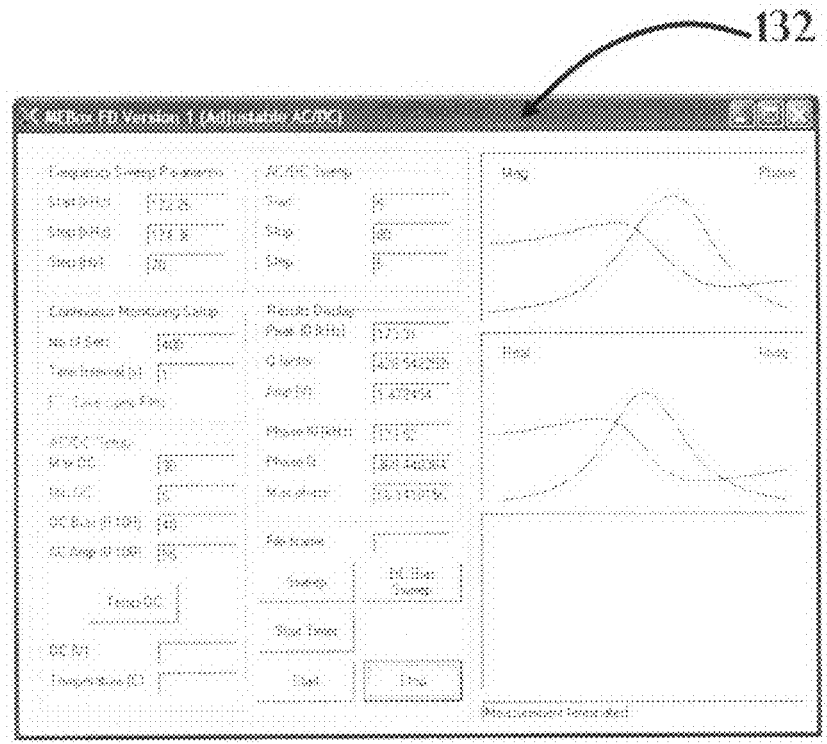
FIG. 15 The graphical user interface (GUI) such as may be used on display screen 132 using suitable user interface graphics.
Figure 20:
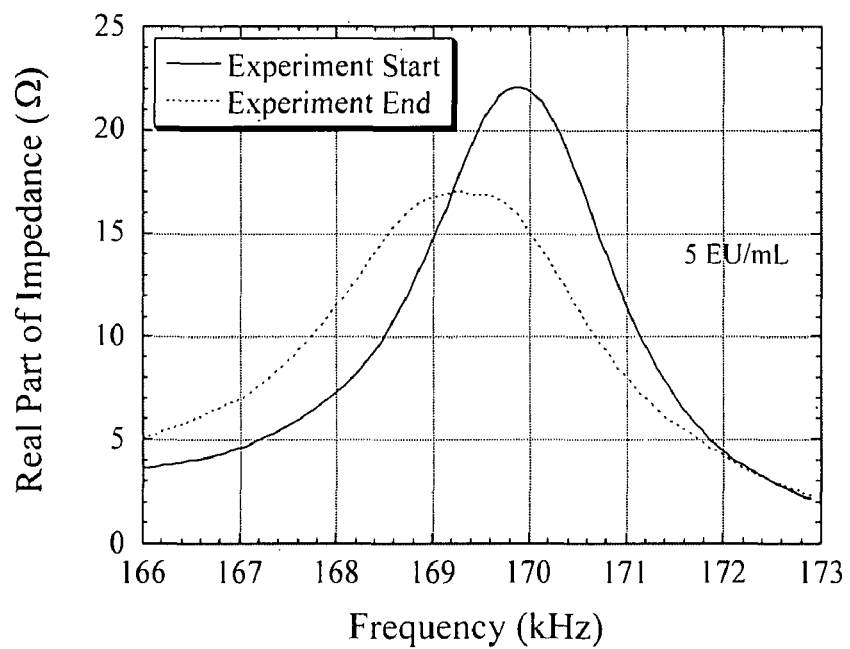
FIG. 20 A graphical representation of the real part of the measured impedance spectrum at the beginning ("start") and "end" of an experiment performed, by way of example, with an endotoxin concentration of 5 EU/ml.

For purposes of testing, the sensor was first inserted into an endotoxin-free test tube (8.7 mm in diameter, 75 mm in length), followed by the addition of 1 ml of test sample, and then 2 vials of PYROGENT Single Test Kit (LAL assay). The mixture was stirred with a vortexer for 1 minute, and then inserted into the interrogation coil of the ME sensor-reader (FIG. 14). Next, the software was launched to interrogate the resonance frequency and amplitude of the sensor every 5 seconds. FIG. 20 includes plots of the real part of the measured impedance at the beginning and end of an experiment with an endotoxin concentration of 5 EU/ml. The resonance frequency decreases from 169.87 kHz to 169.27 kHz, a decrease of 0.35%; the maximum impedance amplitude decreases from 22.07 Ω to 16.89 Ω during the experiment, a 23.5% change. To optimize sensitivity, changes in maximum amplitude were correlated with viscosity changes associated with the LAL assay. Specifically, the sensor response is expressed as the maximum amplitude change, obtained by dividing the maximum amplitude (amplitude at resonance frequency) by the initial maximum amplitude (resonance amplitude at the beginning of the experiment).

Figure 21:
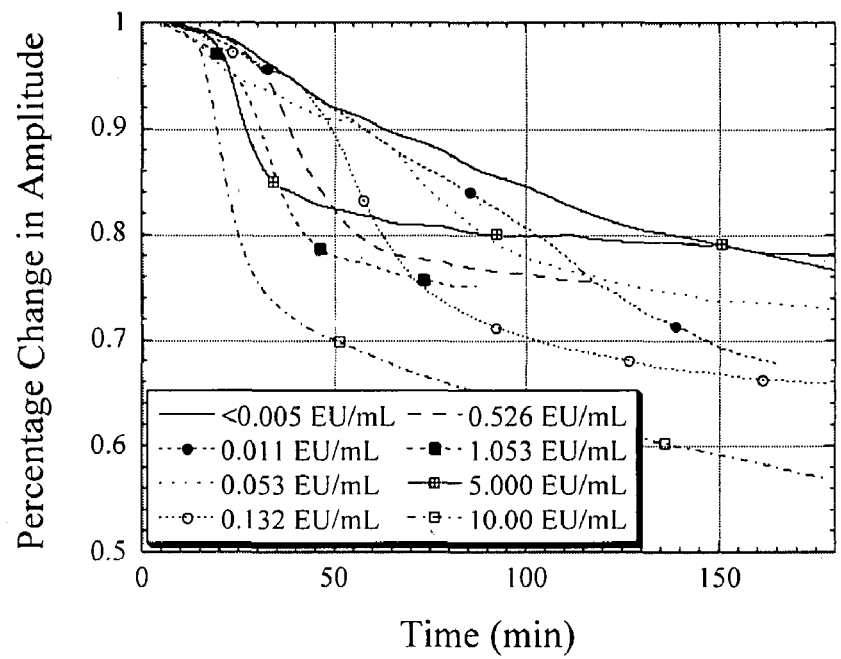
FIG. 21 A graphical representation showing a decrease in maximum amplitudes for sensor elements immersed in an LAL assay mixed with endotoxin of different concentrations.
Figure 22:
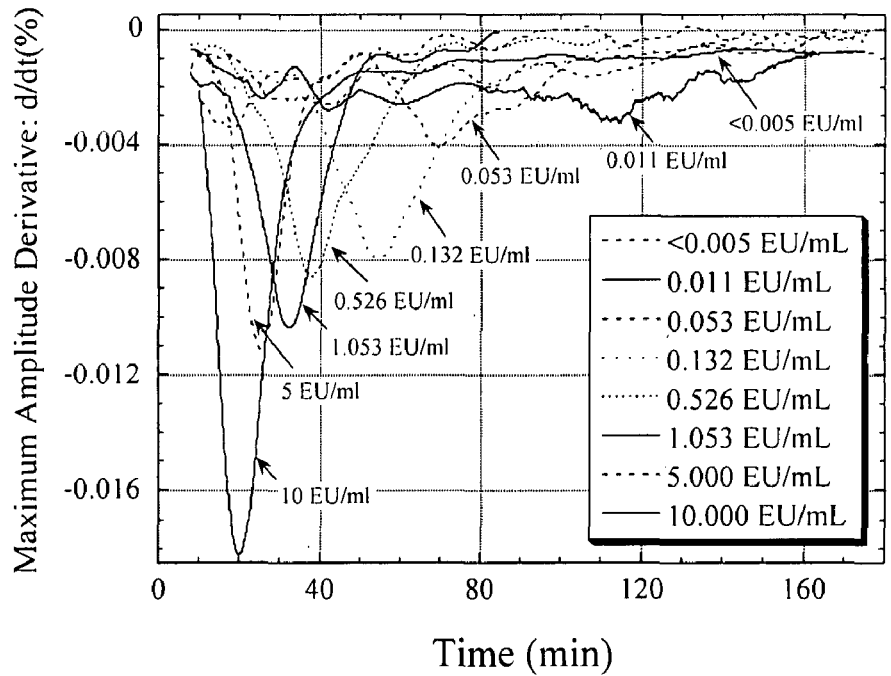
FIG. 22 A graphical representation showing the first derivative of the maximum amplitude-time curves in FIG. 21.
Figure 23:
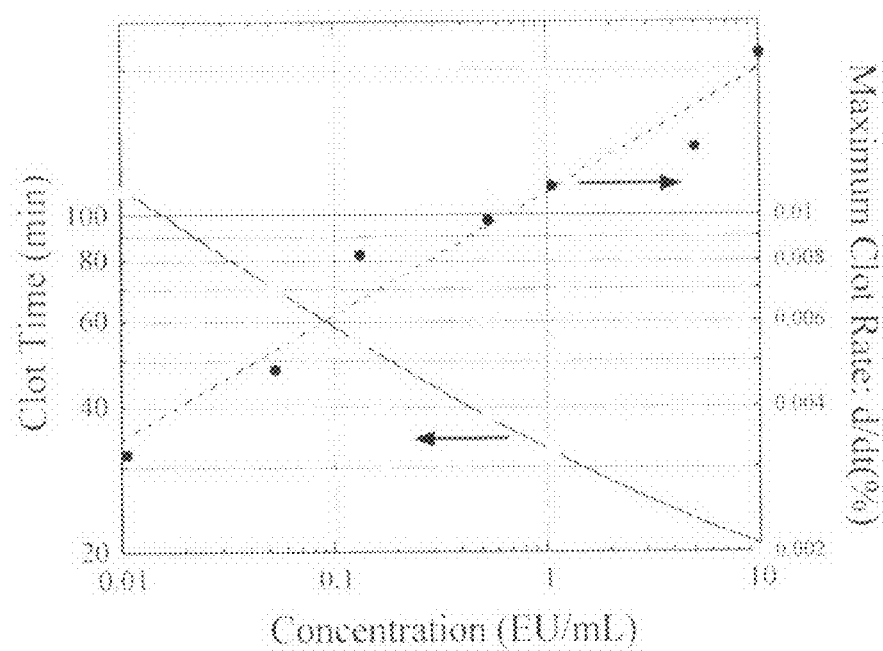
FIG. 23 A graphical representation showing the change in initial clot time and maximum clot rate as a function of endotoxin concentration.

FIG. 21 includes comparison plots illustrating the decrease in maximum amplitudes for sensors immersed in the LAL assay mixed with endotoxin of different concentrations. The results consistently show that the higher the concentration the faster coagulation occurs, and the faster the rate of coagulation. However, the total change in amplitude does not correlate well with endotoxin concentration. The inconsistency between the endotoxin concentration and the total amplitude change is likely due to the inhomogeneity of the clot that results in uneven adhesion on the sensor surface. Visual inspection of a 'clotted' LAL assay shows no solid gel surrounding the sensor but instead a sparse gel-like matrix non-uniformly attached to the sensor surface. As a result, the vibration of the sensor does not solely depend on the clot density, but also how the clot is attached on the sensor surface (which could be enhanced by selective coating of the magnetoelastic sensor with a clot-adhesion promoting compound). Although the total amplitude change could not accurately be used for quantifying endotoxin concentration in our preliminary results, we found that the clot-rate and time-to-clot of the sensor response are closely related to the endotoxin level. FIG. 22 shows the first derivative of the curves seen in FIG. 21; in each curve, we can determine the maximum clot rate (the minimum point of the first derivative), as well as the clot time, defined as the-time that corresponds to the maximum clot rate. FIG. 23 plots the maximum clot rate and clot time as a function of endotoxin concentration. The figure shows that the maximum clot rate is proportional to the endotoxin concentration, while the clot time is inversely proportional to the concentration. By curve-fitting the clot time curve with a power equation (y=a+b x$^c$), an almost perfect least-square fit can be obtained with coefficients a=10.42, b=22.28 and c=−0.3341, with a proportional variance R$^2$ of 0.9998. Conversely, the least-square fit coefficients for the maximum clot rate are a=0, b=0.01108 and c=0.2256, and R$^2$ is 0.9389. These results indicate a strong correlation between the maximum clot rate and clot time with the endotoxin concentration. Using a LAL gel-clot assay with a sensitivity of 0.06 EU/ml, the magnetoelastic sensor can detect the presence of endotoxin at 0.0105 EU/ml in, generally, several tens of minutes. The endotoxin-sensitivity of the magnetoelastic system can be further increased by coating the metallic sensor with a thin hydrophilic coating prior to use.

EXAMPLE 03

Example Application #2: Determination of Blood Clotting Time

Figure 24:
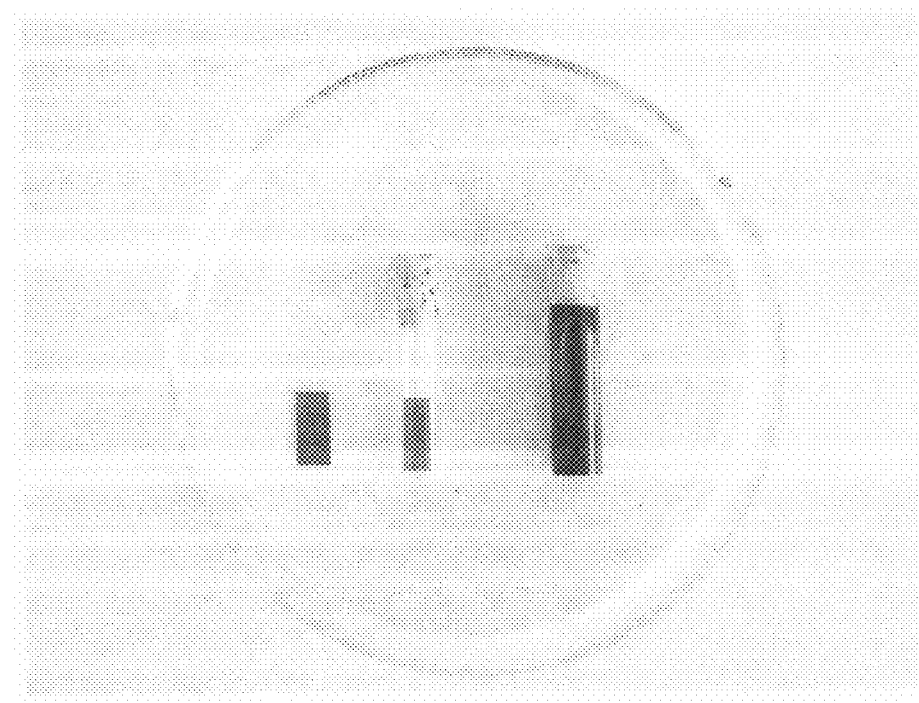
FIG. 24 Digital picture of a magnetoelastic sensor element (far left), a sensor put in a vial (middle shape), and the vial filled with mammalian blood (far right).

In addition to the endotoxin detection, the ME box has been tested to monitor mammalian blood coagulation. When monitoring blood coagulation, a magnetoelastic sensor was immersed in bovine blood within a small vial. The vial was inserted into the solenoid coil, and the sensor signal amplitude was tracked as a function of time. As the blood coagulated around the sensor, it damped the sensor vibration, thus reducing the signal amplitude. FIG. 24 shows the sensor, 12.7 mm×6 mm×28 μm, the sensor in vial, and the sensor in vial filled with bovine blood. FIG. 25 shows the change in sensor vibration amplitude with time.

An analogous blood coagulation curve was obtained using the transient ring-down threshold-crossing counting technique in applicants' earlier patented work: The impedance analysis technique resulted in a 'cleaner' curve. The impedance analysis technique measures the forced vibration of the sensor during a steady sine wave excitation, as opposed to the threshold-crossing counting technique, which measures the free vibration of the sensor after an ac excitation is turned off. This is depicted by FIG. 26: during an ac excitation, a sensor element is forced (labeled "forced vibration") to vibrate at the excitation frequency and the vibration eventually reaches saturation (steady-state) if the excitation is sufficiently long; when the excitation is off, the sensor element will continue to vibrate at resonance frequency until the energy imparted by the excitation dissipates away (as labeled, "free response"). This free response is a transient oscillation with an exponential decay in amplitude. The accuracy of applicants' patented technique for threshold-crossing counting is directed to the existence of this transient oscillation. As the sensor becomes increasingly damped, such as occurs in clotting blood, the transient oscillation decays quickly, resulting in lower signal-to-noise ratio. In contrast, the unique impedance analysis technique contemplated, herein, is directed to the sensor element excitation at steady-state.

The unique impedance analysis technique for characterizing magnetoelastic sensors described includes, by way of example only, an electronic implementation: Please see FIGS. 7 at 100 and 27 at 200. The electronic implementation includes circuitry that, when interfaced with a microprocessor, is capable of characterization of a sensor(s) by obtaining a typical impedance spectrum (20 kHz range with a frequency resolution of 100 Hz) in about one second. Implementation may be done by intercommunication of the microcontroller directly with a user interface, regardless of whether a PC is also employed. Implementation may include communication via serial communication (e.g., RS232) port, with a computerized device (e g., personal computer/PC 130, FIG. 14) to facilitate data processing and storage. The impedance analysis technique is directed to reaching steady-state vibration of the sensor element under excitation, rather than depending on applicants' prior threshold-crossing counting technique directed to the 'ring-down' of a transient vibration. In highly-damped (i.e., viscous) fluids, such as clotting blood, the instant unique impedance analysis technique is quite suitable for tracking the signal amplitude.

While certain representative embodiments and details have been shown for the purpose of illustrating features of the invention, those skilled in the art will readily appreciate that various modifications, whether specifically or expressly identified herein, may be made to these representative embodiments without departing from the novel core teachings or scope of this technical disclosure. Accordingly, all such modifications are intended to be included within the scope of the claims. Although the commonly employed preamble phrase "comprising the steps of" may be used herein, or hereafter, in a method claim, the applicants do not intend to invoke 35 U.S.C. §112 ¶6 in a manner that unduly limits rights to its innovation. Furthermore, in any claim that is filed herewith or hereafter, any means-plus-function clauses used, or later found to be present, are intended to cover at least all structure(s) described herein as performing the recited function and not only structural equivalents but also equivalent structures.

What is claimed is:

1. Circuitry for characterizing a resonant behavior response of a magnetoelastic sensor element during exposure to an excitation field generated by an interrogation coil, the circuitry comprising:
   (a) an excitation circuit for providing an AC excitation signal to the coil;
   (b) a receive circuit for measuring a steady state total sensor signal from the coil with the magnetoelastic sensor element positioned within the excitation field;
   (c) a phase detection circuit for detecting phase of said steady state total sensor signal so measured; and
   (d) a processing unit for determining:
      (i) a total measured impedance spectrum from said steady state total sensor signal so measured, and
      (ii) a plurality of magnitude values representing the real part of a reconstructed impedance spectrum characterizing the resonant behavior response of the sensor element, wherein
      (iii) said reconstructed impedance spectrum is calculated by subtracting an impedance generally attributable to the coil during said providing said AC excitation signal, from said steady state total measured impedance.

2. The circuitry of claim 1:
   (a) further comprising a digital synthesis circuitry to aid in said providing said AC excitation signal, and a microprocessor unit comprising said processing unit; and
   (b) wherein said providing said AC excitation signal in conjunction with said measuring said total sensor signal, comprises:
      (i) performing a frequency sweep over a selected range of frequencies, and
      (ii) for each of a plurality of consecutive frequencies within said selected range, measuring a coil voltage magnitude and phase across the coil and applying the expression $Z_t(\omega)=V(\omega)/I(\omega)$; wherein $I(\omega)$ represents said AC excitation signal as a current applied to the coil, $V(\omega)$ represents a voltage measured across the coil with the sensor element positioned within the excitation field, and $Z_t(\omega)$ represents said total measured impedance.

3. The circuitry of claim 1, in use for sensing to obtain information about an environment within which the magnetoelastic sensor element is immersed as positioned within the excitation field.

4. The circuitry of claim 3 wherein said reconstructed impedance spectrum is calculated by subtracting a real resistance of said impedance generally attributable to the coil from a real part of said total measured impedance, and subtracting an imaginary reactance of said impedance generally attributable to the coil from an imaginary part of said total measured impedance.

5. The circuitry of claim 3:
   (a) further comprising DC biasing circuitry in communication with the coil for providing a biasing field to which the sensor element is also exposed, and a microprocessor unit comprising said processing unit; and
   (b) wherein said position within the excitation field comprises the sensor element positioned within a spacing created by a winding of the coil.

6. The circuitry of claim 3 wherein:
   (a) said phase detection circuit comprises circuitry for generating a reference signal against which said phase of said total sensor signal is compared to find a phase difference there-between; and
   (b) said providing said AC excitation signal in conjunction with said measuring said total sensor signal, comprises:
      (i) performing a frequency sweep over a selected range of frequencies, and
      (ii) for each of a plurality of consecutive frequencies within said selected range, measuring a coil voltage magnitude and phase across the coil.

7. The circuitry of claim 1 wherein:
   (a) said reconstructed impedance spectrum is calculated by subtracting a value for resistance of the coil from a real part of said total measured impedance, and subtracting an imaginary reactance of said impedance generally attributable to the coil from an imaginary part of said total measured impedance; and
   (b) a relative maximum of said plurality of magnitude values so determined for said reconstructed impedance spectrum represents the response at a resonance frequency of the sensor element.

8. The circuitry of claim 7 in use for sensing to obtain information about an environment within which the sensor element is immersed as positioned within the excitation field.

9. A method for characterizing a resonant behavior response of a magnetoelastic sensor element during exposure to an excitation field generated by an interrogation coil, the method comprising the steps of:
   (a) providing an AC excitation signal to the coil;
   (b) measuring a steady state total sensor signal from the coil with the magnetoelastic sensor element positioned within the excitation field within a spacing created by a winding of the coil;
   (c) detecting the phase of said steady state total sensor signal so measured; and
   (d) automatically determining:
      (i) a total measured impedance spectrum from said steady state total sensor signal so measured, and (ii) a plurality of magnitude values representing the real part of a reconstructed impedance spectrum characterizing the resonant behavior response of the sensor element, and (iii) calculating said reconstructed impedance spectrum by subtracting an impedance generally attributable to the coil during said providing said AC excitation signal, from said steady state total measured impedance.

10. The method of claim 9 wherein the magnetoelastic sensor element is in use for sensing to obtain information about an environment within which the sensor element is immersed as positioned within the excitation field.

11. The method of claim 10 wherein said calculating of said reconstructed impedance spectrum further comprises subtracting a real resistance of said impedance generally attributable to the coil from a real part of said total measured impedance, and subtracting an imaginary reactance of said impedance generally attributable to the coil from an imaginary part of said total measured impedance.

12. The method of claim 9 wherein:
(a) said detecting the phase further comprises generating a reference signal against which said phase of said total sensor signal is compared to find a phase difference there-between; and
(b) said providing said AC excitation signal in conjunction with said measuring said total sensor signal, comprises:
    (i) performing a frequency sweep over a selected range of frequencies, and
    (ii) for each of a plurality of consecutive frequencies within said selected range, measuring a coil voltage magnitude and phase across the coil.

13. The method of claim 9:
(a) wherein said step of automatically determining further comprises calculating said reconstructed impedance spectrum by subtracting a value for resistance of the coil from a real part of said total measured impedance, and subtracting an imaginary reactance of said impedance generally attributable to the coil from an imaginary part of said total measured impedance; and
(b) further comprising the step of using data including a relative maximum of said plurality of magnitude values so determined for said reconstructed impedance spectrum, for sensing to obtain information about an environment within which the sensor element is immersed as positioned within the excitation field.

14. The method of claim 9 further comprising the steps of:
(a) digitally synthesizing said AC excitation signal prior to providing to the coil;
(b) generating a DC biasing field within said spacing created by the coil winding; and
(c) wherein said providing said AC excitation signal in conjunction with said measuring said total sensor signal, comprises performing a frequency sweep over a selected range of frequencies.

15. A non-transitory computer readable storage medium having stored thereon, program code for causing a computer processor to execute instructions for characterizing a resonant behavior response of a magnetoelastic sensor element during exposure to an excitation field generated by an interrogation coil, the program code comprising:
(a) a first program sub-code comprising instructions for providing an AC excitation signal to the coil;
(b) a second program sub-code comprising instructions for measuring a steady state total sensor signal from the coil with the sensor element positioned within the excitation field within a spacing created by a winding of the coil;
(c) a third program sub-code comprising instructions for detecting the phase of said steady state total sensor signal; and
(d) a fourth program sub-code comprising instructions for automatically determining:
    (i) a total measured impedance spectrum from said steady state total sensor signal so measured, and
    (ii) a plurality of magnitude values representing the real part of a reconstructed impedance spectrum characterizing the resonant behavior response of the sensor element, and
    (iii) instructions for calculating said reconstructed impedance spectrum by subtracting an impedance generally attributable to the coil during said providing said AC excitation signal, from said steady state total measured impedance.

16. The non-transitory computer readable storage medium having stored thereon, the program code of claim 15 wherein the magnetoelastic sensor element is in use for sensing to obtain information about an environment within which the sensor element is immersed as positioned within the excitation field.

17. The non-transitory computer readable storage medium having stored thereon, the program code of claim 16 wherein said fourth program sub-code instructions for calculating comprises instructions for subtracting a real resistance of said impedance generally attributable to the coil from a real part of said total measured impedance, and subtracting an imaginary reactance of said impedance generally attributable to the coil from an imaginary part of said total measured impedance.

18. The non-transitory computer readable storage medium having stored thereon, the program code of claim 15 wherein
(a) said third program sub-code further comprises instructions for generating a reference signal against which said phase of said total sensor signal is compared to find a phase difference there-between; and
(b) said first and second program sub-code operate integrally and further comprise instructions for providing said AC excitation signal in conjunction with said measuring said total sensor signal, including instructions for:
    (i) performing a frequency sweep over a selected range of frequencies, and
    (ii) for each of a plurality of consecutive frequencies within said selected range, measuring a coil voltage magnitude and phase across the coil.

19. The non-transitory computer readable storage medium having stored thereon, the program code of claim 15:
(a) wherein said fourth program sub-code further comprises instructions for calculating said reconstructed impedance spectrum by subtracting a value for resistance of the coil from a real part of said total measured impedance, and subtracting an imaginary reactance of said impedance generally attributable to the coil from an imaginary part of said total measured impedance; and
(b) further comprising a fifth program sub-code for using data including a relative maximum of said plurality of magnitude values so determined for said reconstructed impedance spectrum, for sensing to obtain information about an environment within which the sensor element is immersed as positioned within the excitation field.

20. A method for characterizing a resonant behavior response of a magnetoelastic sensor element during exposure to an excitation field generated by an interrogation coil, the method comprising the steps of:
(a) measuring a steady state total sensor signal from the coil with the magnetoelastic sensor element positioned within the excitation field within a spacing created by a winding of the coil; and
(b) automatically determining:
  (i) a total measured impedance spectrum from said steady state total sensor signal so measured, and
  (ii) a plurality of magnitude values representing the real part of a reconstructed impedance spectrum characterizing the resonant behavior response of the sensor element, wherein
  (iii) said reconstructed impedance spectrum is calculated by subtracting an impedance generally attributable to the coil during said providing said AC excitation signal, from said steady state total measured impedance.

* * * * *